United States Patent
Lokeshwar et al.

(10) Patent No.: US 6,350,571 B1
(45) Date of Patent: Feb. 26, 2002

(54) METHODS FOR DETECTION AND EVALUATION OF BLADDER CANCER

(76) Inventors: Vinata B. Lokeshwar, 12615 SW. 112 Ct., Miami, FL (US) 33176; Henry T. Pham, 6550 Mapleridge, Suite 122, Houston, TX (US) 77081

(*) Notice: Subject to any disclaimer, the term of this patent is extended or adjusted under 35 U.S.C. 154(b) by 0 days.

(21) Appl. No.: 09/265,604

(22) Filed: Mar. 10, 1999

Related U.S. Application Data

(63) Continuation-in-part of application No. 08/790,821, filed on Jan. 30, 1997, now abandoned.
(60) Provisional application No. 60/010,976, filed on Feb. 1, 1996.

(51) Int. Cl.$^7$ .......................... C12Q 1/00; G01N 33/53; G01N 33/573; G01N 33/48
(52) U.S. Cl. .............................. 435/4; 435/7.1; 435/7.4; 435/7.72; 435/810; 436/64
(58) Field of Search .......................... 435/4, 810, 7.1, 435/7.4, 7.72; 436/64

(56) References Cited

U.S. PATENT DOCUMENTS

| | | |
|---|---|---|
| 4,474,893 A | 10/1984 | Reading |
| 4,722,899 A | 2/1988 | Hamaoka et al. ......... 435/172.2 |
| 4,826,776 A | 5/1989 | Brandt et al. ............... 436/501 |
| 5,019,498 A | 5/1991 | Chicibu ...................... 435/7.5 |
| 5,102,787 A * | 4/1992 | Sasamata et al. |
| 5,264,370 A | 11/1993 | Aken ......................... 436/501 |
| 5,359,031 A | 10/1994 | Zhau et al. |
| 5,378,637 A | 1/1995 | Goldberg .................... 436/501 |
| 5,541,076 A | 7/1996 | Houghton et al. .......... 435/7.23 |
| 5,591,830 A | 1/1997 | Van Aken et al. ....... 530/388.5 |

OTHER PUBLICATIONS

Harzmann et al., Curr.Probl.Clin.Biochem., 1979, v9, (abstract only).*
Tockman et al., Cancer Res., 1992, 52:2711s–2718s.*
Pham, et al., Abstr.#1214, The J. of Urology, vol. 155, May 1996, Suppl. p. 614A.
Delpech, et al, Analytical Biochemistry, vol. 49, 1985, pp. 555–565.
S. Baba, The Japanese Journal of Urology, vol. 74 No. 8, Aug. 1983, pp. 1352–1361 Abstract only.
M. D'Hallewin, et al., The Journal of Urology, vol. 155, Feb. 1996, pp. 475–476.
S. Kumar, et al., Int'l J. Cancer, vol. 44, 1989, pp. 445–448.
R. Y. Lin, et al., Journal of Pediatric Surgery, vol. 30, No. 2, Feb. 1995, pp. 304–308.
V.B. Lokeshwar, et al., Cancer Research, vol. 56, Feb. 1996, pp. 651–657.
V.B. Lokeshwar, et al., Cancer Research, vol. 57, Feb. 1997, pp. 773–777.
E.M. Messing, et al., The journal of Urology, vol. 154, Jul. 1995, pp. 57–61.
M. DeSalegui, et al., Archives of Biochem. Biophys., 121, 1967, pp. 548–554.
M.F. Sarosdy, et al., The Journal of Urology, vol. 154, Aug. 1995, pp. 379–384.
M.S. Soloway, et al., The Journal of Urology, vol. 156, Aug. 1996, pp. 363–367.
M. Stern, et al., Journal of National Cancer Inst., vol. 83, No. 21, Nov. 1991, pp. 1569–1574.
M. Stern, et al., Matrix, vol. 12, 1992, pp. 397–403.
A. Tengblad, Biochima et Biophica Acta, 578, 1979, pp. 281–289.
Urology Grand Rounds, vol. 1, 1996, p. 15.
Lokeshwar, et al., Abstr.#1207, The J. of Urology, vol. 155, No. 5, May 1996, Suppl. p. 613A.
Seaver, et al., Genetic Engineering News, vol. 14, No. 14, 1994, pp. 10 and 21.
Sevier, et al., Clinical Chemistry, vol. 27, No. 11, 1981, pp. 1797–1806.

* cited by examiner

*Primary Examiner*—Anthony C. Caputa
*Assistant Examiner*—Gary B Nickol
(74) *Attorney, Agent, or Firm*—Ted W. Whitlock

(57) ABSTRACT

The present invention relates to novel methods for detecting and evaluating bladder cancer. The methods of the present invention are based on the discovery that normalized amounts of hyaluronic acid (HA) and hyaluronidase (HAase) are diagnostic markers for the detection of bladder cancer, evaluation of its grade, monitoring of the efficacy of its treatment, and tumor recurrence.

8 Claims, 13 Drawing Sheets

METHODS FOR DETECTION AND EVALUATION OF BLADDER CANCER

CROSS-REFERENCE TO RELATED APPLICATIONS

This application is a continuation-in-part of U.S. application Ser. No. 08/790,821, filed Jan. 30, 1997, now abandoned the disclosure of which is incorporated herein by reference, which is a continuation-in-part of U.S. Provisional Appln. No. 60/010,976, filed Feb. 1, 1996.

BACKGROUND OF THE INVENTION

1. Field of the Invention

This invention relates to novel methods for detecting and evaluating bladder cancer, utilizing hyaluronic acid (HA) and hyaluronidase (HAase).

2. Description of Related Art

Bladder carcinoma is the most common cancer of the urinary tract, accounting for 51,000 new cases and 11,000 deaths each year in the United States. Transitional cell carcinomas (TCCs) account for ≈90% of the bladder tumors. These tumors are heterogeneous in their ability to progress. For example, some TCCs behave in a benign fashion (low-grade, G1 tumors) whereas others are intermediate (G2 tumors) to highly aggressive (G3 tumors and carcinoma in situ (CIS)). The high-grade tumors generally metastasize quickly; indeed, at the time of clinical presentation (e.g., hematuria, irritative voiding symptoms etc.), invasive disease already exists for many patients with high-grade bladder tumors.

The two most important prognostic factors for TCCs are grade and stage (which indicates the depth of invasion) (American Joint Committee on Cancer: Staging of cancer at genito-urinary sites. In: Manual for Staging Cancer, $3^{rd}$ edition, pp. 194–195, J. B. Lippincott Co., Philadelphia, 1988). Low-grade (G1) tumors are mostly confined to the mucosa (stage Ta) and have a <2% chance of progression (Heney, Natural history of superficial bladder cancer. Urol. Clin. North Am., 19: 429–435, 1992; Heney and Flanagan, Superficial bladder cancer progression and recurrence. J. Urol., 130: 1083–1086, 1983). Intermediate-grade (G2) tumors range from being non-invasive (Ta) to invasive (stages T1–T4). The G2, Ta tumors have ~11% chance of progression (Heney, Natural history of superficial bladder cancer. Urol. Clin. North Am., 19: 429–435, 1992). With the exception of carcinoma in situ (CIS), most high-grade tumors are initially detected at least at stage T1 (invading lamina propria) and are thus invasive. Muscle invasion (stage T2) by the tumor is ominous, as 50% of these patients develop distant metastasis within two years of diagnosis despite radical surgery, and 60% of them die within 5 years, however treated (Heney and Flanagan, Superficial bladder cancer progression and recurrence. J. Urol., 130: 1083–1086, 1983; Friedell et al., Summary of workshop on carcinoma-in-situ of the bladder. J. Urol., 136: 1047–1048, 1986; Soloway, Invasive bladder cancer: Selection of primary treatment. Semin. Oncol., 17: 551–554, 1990). Due to the malignant nature of high-grade TCCs, their early detection prior to muscle invasion, is crucial for a favorable prognosis.

Thus, it is not only important to detect the presence of tumor early, it is also crucial to identify the high-grade tumors which present with such a grim prognosis. Tumor recurrence is also a characteristic of bladder carcinoma. Therefore, despite a complete remission of the original tumor, patients must be closely followed in order to monitor the treatment efficacy and recurrence (Heney, Natural history of bladder cancer. Urol. Clin. North Am., 19: 429–433, 1992).

The current methods for bladder cancer detection involve cystoscopy, bladder washings, and biopsy. These procedures are invasive and require some form of anesthesia. Urine cytology use is possible but its specificity is low due to its subjective nature. A few other markers such as DNA ploidy, p53 mutations, microsatellite DNA, β-glucuronidase, basic-FGF levels, autocrine motility factor receptor etc. have been shown to be associated with bladder cancer (Sidransky and Messing, Molecular genetics and biochemical mechanisms in bladder cancer. Urol. Clin. North Am., 19: 629–639, 1992; Mao et al., Molecular detection of primary bladder cancer by microsatellite DNA. Science, 271: 659–662, 1996; Nguyen et al., Elevated levels of the angiogenic peptide basic fibroblast growth factor in urine of bladder cancer patients. J. Natl. Cancer Inst., 85: 241–242, 1993; Esrig et al., Accumulation of nuclear p53 and tumor progression in bladder cancer. N. Engl. J. Med., 331: 1259–1264, 1994; Ho, Urinary β-glucuronidase in screening and follow up of primary urinary tract malignancy. J. Urol., 154: 1335–1338, 1995; Korman et al., Autocrine motility factor receptor as a possible urine marker for transitional cell carcinoma of the bladder. J. Urol., 154: 347–349, 1995). However, most of these have not yet been used clinically as diagnostic markers.

Currently, three non-invasive diagnostic tests for bladder cancer are under investigation in the United States. The hematuria home screening test has high sensitivity but low specificity due to the wide spectrum of benign genito-urinary (GU) conditions (kidney stones, benign prostatic hyperplasia etc) which give rise to false positives (Britton et al., A community study of bladder cancer screening by the detection of occult urinary bleeding. J. Urol., 148:788–790, 1992; Messing et al., Hematuria home screening: Repeat testing results. J. Urol., 154: 57–61, 1995). The second test is the Bard BTA Latex agglutination assay. A multi-center trial for this test was conducted in the United States to monitor bladder tumor recurrence. The results show that the sensitivity of this test to detect bladder tumors and, more importantly high-grade TCCs, is only ≈40–50% (Sarosdy et al., Results of a multicenter trial using the BTA test to monitor for and diagnose recurrent bladder cancer, J. Urol., 154: 379–384, 1995; U.S. Pat. No. 5,264,370). In another multicenter study involving 90 patients and the third test, Soloway et al. have shown that the NMP22 test has an overall sensitivity of 70% to detect bladder tumor recurrence (Soloway et al., Use of a new tumor marker NMP22 in the detection of occult or rapidly recurring transitional cell carcinoma of the urinary tract following surgical treatment. J. Urol., 156: 363–367, 1996). Thus, to date, no non-invasive test exists that can detect bladder tumor and/or evaluate its grade with high sensitivity and specificity.

With the above problems in the art in mind, the inventors have developed non-invasive methods to detect bladder cancer by measuring the levels of certain "molecular determinants" specifically expressed in the biological fluids (such as urine specimens) of bladder cancer patients. More particularly, the methods of the invention are based on the inventors' discovery that levels of hyaluronic acid and hyaluronidase in a sample of biological fluid, especially urine, are associated with the presence and grade of bladder cancer.

Hyaluronic acid (also known in the art as hyaluronate and hyaluronan, and abbreviated as HA), is a glycosaminoglycan comprising a straight unbranched polysaccharide chain with alternating units of N-acetyl-D-glucosamine and D-glucuronic acid. HA is present ubiquitously in various types of biological material, including both bacteria and animals. In humans, HA is found in high concentrations in umbilical cords, vitreous humor of the eyes, cartilage and synovial fluid. Small amounts of HA are present in CSF, lymph, blood, serum and urine. Levels of HA have been associated with diseases such as rheumatoid arthritis, liver cirrhosis, and Wilms' tumor. HA is associated with non-specific tumors in general, but its use has not been applied heretofore to the discovery, therapy and management of particular clinical tumors.

HA has been known to play a role in several pathophysiological conditions including cancer. For example, HA levels have been shown to be elevated in certain animal tumor models (e.g., rabbit V2 carcinoma, Knudson et al., The role and regulation of tumor associated hyaluronan. In: The Biology of Hyaluronan (J. Whelan, ed.), pp. 150–169, New York, Wiley Chichister (Ciba Foundation Symposium 143), 1989) and human cancers (e.g., lung, Wilms' tumor, breast, etc., Knudson et al., ibid.).

In tumor tissues, HA expands upon hydration opening spaces for tumor cell migration (Knudson et al., The role and regulation of tumor associated hyaluronan. In: The Biology of Hyaluronan (J. Whelan, ed.), pp. 150–169, New York, Wiley Chichister (Ciba Foundation Symposium 143), 1989). Furthermore, tumor cells migrate on HA matrix by interacting through certain cell surface receptors (e.g., CD44; Thomas et al., Migration of human melanoma cells on hyaluronate is related to CD44 expression. J. Invest. Dermatol., 100: 115–120, 1993). HA also forms a halo around tumor cells that protects them against immune surveillance (Hobarth et al., Topical chemoprophylaxis of superficial bladder cancer by mitomycin C and adjuvant hyaluronidase. Europ. Urol., 21: 206–210, 1992). More recently, small fragments of HA (~3–25 disaccharide units) have been shown to promote angiogenesis (West et al., Angiogenesis induced by degradation products of hyaluronic acid. Science, 228: 1324–1326, 1985; West and Kumar, The effect of hyaluronate and its oligosaccharides on endothelial cell proliferation and monolayer integrity. Exp. Cell Res., 183: 179–196, 1989). Earlier work from one of the inventors has shown that an HA fragment of 10–15 disaccharide units (F1 fragment), stimulates proliferation of bovine aortic endothelial cells. A similar sized fragment has also been shown to promote endothelial cell migration and tubule formation (Banarjee and Toole, Hyaluronan binding protein in endothelial cell morphogenesis. J. Cell Biol., 119: 643–652, 1992).

In the present application, the inventors measure the HA levels in the urine of normal individuals and bladder cancer patients, and in the extracts prepared from normal bladder and tumor tissues, as discussed below. Also as discussed below, the inventors examine the profile of HA species present in the urine of normal individuals, bladder cancer patients, and patients with other genito-urinary (GU) conditions. In addition, they determine whether the HA or HA fragments present in the urine affect the proliferation of human endothelial cells.

The inventors disclose in the present application that the urinary HA levels of bladder cancer patients with G1, G2 and G3 tumors are significantly elevated (for instance, 4–9 fold elevation) as compared to those of normal individuals and patients with other genito-urinary (GU) conditions ($P<0.001$). As discussed below, the inventors also discovered that a comparison of pre- and post-treatment urinary HA levels can be used to monitor treatment efficacy. For example, elevated post-treatment urinary HA levels are indicative of persistent bladder cancer and possible relapse at later time. The urinary HA levels are also useful to monitor bladder cancer recurrence during follow-up visits subsequent to the initial treatment. The increase in urinary HA concentration is a direct correlate of the elevated tumor-associated HA levels, because the HA levels are also elevated (for instance, 3–5 fold) in bladder tumor tissues ($P<0.001$). The profiles of urinary HA species of normal individuals and bladder cancer patients are different. While only the intermediate size HA species are found in the urine of normal and low-grade bladder tumor patients, the urine of high-grade bladder cancer patients contains both the high molecular mass and the small angiogenic HA fragments.

The inventors also disclose in the present application that these urinary HA fragments stimulate a mitogenic response (for instance, 2–4 fold) in primary human microvessel endothelial cells, suggesting that the small HA fragments may regulate tumor angiogenesis by modulating endothelial cell functions. The inventors hypothesized that small HA fragments in the urine of high-grade bladder cancer patients may indicate that a hyaluronidase activity is present in the urine of these patients.

Hyaluronidase (HAase) is an endoglycosidic enzyme that degrades HA by hydrolyzing the N-acetylglucosaminic bonds in HA. The limited degradation of HA by hyaluronidase results in the generation of HA fragments of specific lengths (~3–25 disaccharide units) that are angiogenic (West et al., Angiogenesis induced by degradation products of hyaluronic acid. Science, 228: 1324–1326, 1985). In vertebrates, hyaluronidases can be categorized into two classes, those active at neutral pH (pH optimum 5.0), and those active at acidic pH (pH 3.5–4.0) (Roden et al., Enzymatic pathways of hyaluronan catabolism. In: The Biology of hyaluronan, (J. Wh.elan, ed.), pp. 60–86, New York, Wiley Chichister (Ciba Foundation Symposium 143), 1989; West et al., ibid.; Gold, Purification and properties of hyaluronidase from human liver. Biochem. J., 205: 69–74, 1982; Fraser and Laurent, Turnover and metabolism of Hyaluronan. in: Biology of Hyaluronan, (J. Whelan, ed.), pp. 41–59, New York, Wiley Chichister (Ciba Foundation Symposium 143), 1989; Zhu et al., Molecular cloning of a mammalian hyaluronidase reveals identity with hemopexin, a serum heme-binding protein. J. Biol. Chem., 269: 32092–32097, 1994; Lin et al., A hyaluronidase activity of the sperm plasma membrane protein PH-20 enables sperm to penetrate the cumulus layer surrounding the egg. J. Cell Biol., 125: 1157–1163, 1995). For example, the testicular hyaluronidase is of neutral type whereas the liver hyaluronidase has an acidic pH optimum. The concerted actions of both HA and hyaluronidases are known to play important roles during embryonic development, vasculogenesis, vascular remodeling, immune surveillance and tumor progression (McCormick and Zetter, Adhesive interactions in angiogenesis and metastasis. Pharmacol. Ther., 53: 239–260, 1992; Hobarth et al., Topical chemo-prophylaxis of superficial bladder cancer by mitomycin C and adjuvant hyaluronidase, Eur. Urol., 21: 206–210, 1992; Knudson et al., The role and regulation of tumor-associated hyaluronan. In: The Biology of Hyaluronan (J. Whelan, ed.) pp. 150–169, New York, Wiley, Chichester (Ciba Foundation Symposium 143), 1989; Lin et al., Urinary hyaluronic acid is a Wilms' tumor marker. J. Ped. Surg., 30: 304–308, 1995; Stern et al., Hyaluronidase levels in urine from Wilms' tumor patients. J. Natl. Canc. Inst., 83: 1569–1574, 1991). The inventors have shown that hyaluronidase levels are elevated in prostate cancer and the increase correlates with the aggressiveness of prostate cancer (Lokeshwar et al., Association of hyaluronidase, a matrix-degrading enzyme with prostate cancer progression. Cancer Res., 56: 651–657, 1996).

The inventors disclose in the present application that the urinary HAase levels of bladder cancer patients with G2 and G3 tumors are significantly elevated (for instance, 5–8 fold) as compared to those of normal individuals, patients with G1 tumors and patients with other GU conditions (P<0.001). As discussed below, the inventors also discovered that a comparison of pre- and post-treatment urinary hyaluronidase levels can be used to monitor treatment efficacy. For example, post-treatment elevated urinary hyaluronidase levels are indicative of persistent G2 or G3 bladder tumor and possible relapse at a later time. The urinary hyaluronidase levels are also useful to monitor G2 or G3 bladder tumor recurrence during follow-up visits subsequent to the initial treatment. The increase in urinary hyaluronidase levels is due to the secretion of a tumor-associated hyaluronidase into the urine, as the hyaluronidase levels in G2/G3 tumor tissues are also higher (for instance, about 6–7 fold) than those in normal bladder and G1 tumor tissues (P<0.001). The bladder tumor-associated hyaluronidase activity is distinct from other hyaluronidases, has a pH optimum of 4.3 and is attributed to two proteins of Mr 65 kD (p65) and 55 kD (p55).

Prior to the invention, neither HA nor HAase have been associated with bladder cancer, nor have they been used for the detection or evaluation of bladder cancer. However, using the assay methods of the present invention, HA and HAase can be used in a non-invasive test to detect bladder cancer and evaluate its particular grade.

ELISA-like assays to determine HA concentrations have been described previously. For example, Goldberg et al. (U.S. Pat. No. 5,378,637) have described that HA can be measured in a biological sample by coating a solid support with HA, incubating the sample with a cartilage proteoglycan (which is known to bind HA in any biological material), and then exposing the sample to a coated solid support. The amount of cartilage proteoglycan bound to the solid HA support is determined by anti-keratin sulfate-reactive antibody.

A similar method has been described using pig laryngeal cartilage proteoglycan by Fosang et al. (Matrix, 10: 306–313, 1990). That article describes an ELISA plate-based assay for hyaluronan using biotinylated proteoglycan G1 domain (HA-binding region).

An ELISA-like assay has been described by Stern and Stern (Matrix, 12: 397–403, 1992). That reference describes hyaluronidase determination using biotinylated HA binding protein, mouse anti-keratin sulfate antibody, biotinylated goat anti-mouse IgG and avidin-biotin detection system. Using the same assay, Stern et al. have measured urinary hyaluronidase levels in Wilms' tumor patients (Stern et al., Hyaluronidase levels in urine from Wilms' tumor patients. J. Natl. Canc. Inst., 83: 1569–1574, 1991).

Other hyaluronic acid determination methods are described by Chichibu (U.S. Pat. No. 5,019,498), and Brandt et al. (U.S. Pat. No. 4,826,776).

SUMMARY OF THE INVENTION

The methods of the present invention are based on the discovery that urinary HA and HAase levels are diagnostic markers for the detection of bladder cancer, evaluation of its grade and monitoring of the efficacy of its treatment.

With the invention, the measurements of HA and HAase levels are technically simple, because these are ELISA-like assays. Both assays require only an HA-binding protein, which can be purified in large quantities using a well established procedure (Tengblad, A. Affinity chromatography on immobilized hyaluronate and its application to the isolation of hyaluronate binding proteins from cartilage. Biochim. Biophys. Acta, 578: 281–289, 1979). Both assays are simple, non-invasive yet highly sensitive and specific tests that may be used clinically for bladder cancer detection. The ELISA-like assay for HA measurement (HA test) detects bladder cancer regardless of the tumor grade. The ELISA-like assay for HAase measurement (HAase test) preferentially detects intermediate-grade (G2) to high-grade (G3) bladder tumors.

Since urinary hyaluronidase measurement detects CIS (pre-invasive G3 bladder tumors) as well as G2, Ta tumors, the invention is a better non-invasive method for the early detection of G2 and G3 bladder tumors which present with poor prognosis for the patient.

Accordingly, in one embodiment of this invention bladder cancer is tested for by quantitatively measuring HA in a sample of biological fluid (such as, for instance, a urine specimen) collected from a patient suspected of having bladder cancer. Any conventional assay methodology can be used to determine the presence and measurement of HA, including radioassays, sandwich assays, inhibition assays and the like. However, HA is preferably measured a competitive binding assay. More preferably, the assay of the invention works in the same manner as an ELISA test, but does not make use of antibody completing mechanisms.

For instance, bladder cancer can be detected in an assay method comprising the steps of:

(a) coating a solid support (preferably, microtiter wells) with HA;

(b) contacting and incubating HA binding protein (HABP) with the coated solid support in the presence of a sample of biological fluid (such as a urine sample) collected from a person suspected of having bladder cancer, under conditions such that the HABP is permitted to bind to the HA coated on the solid support and the HA in the sample (if any is present);

(c) determining the amount of HABP bound to the HA coated on the solid support, and determining therefrom the amount of HA present in the sample.

In this embodiment, the coated HA and the HA contained in the sample "compete" to bind with the HABP. Where HA is present in the sample, less HABP will bind to the coated HA, as determined by, for instance, comparison with a standard. In other words, little HABP bound to the coated HA would mean HA present in the sample, which would be indicative of bladder cancer.

The preferred way to determine the amount of HABP bound to the HA coated on the solid support, and determine therefrom the amount of HA present in the sample, is to detect a signal associated with or produced by the bound HABP.

For example, a microtiter plate reader can be used to measure absorbance of colored product as an indirect measure of biotinylated HABP bound to the solid support (avidin-enzyme conjugate and labeled substrate are used to generate the colored product). The maximum absorbance can be obtained by incubating the HA-coated wells with buffer alone in the absence of any HA or HA-containing sample. A standard graph can then be prepared by plotting absorbance versus ng/well or 0.2 ml of HA. Using this standard graph, the HA concentration (ng/ml) in each dilution of the sample can be calculated. From several such determinations the mean HA concentration in each sample can be determined. Protein concentration (mg/ml) of the sample can be determined, for example, by automated analysis or with a protein assay kit (BioRad, Richmond, Calif.). The HA concentrations can be normalized to the protein content and expressed as ng/mg protein.

For example, the calculations for determining urinary HA levels can be as follows: A×dilution factor÷mg/ml urinary protein, where A is ng/ml of HA concentration extrapolated from the standard graph. The HA levels are finally expressed as ng/mg total protein. A low absorbance reading would be indicative of a significant amount of HA in the urine sample, which would itself be indicative of bladder cancer in the patient.

In general, a calculation of more than about 500 ng/mg HA in the sample is indicative of bladder cancer in the patient.

The sensitivity of this method to detect bladder cancer using HA can be about 88% or more (and may be as high as 100%) and the specificity can be about 87% or more (and may be as high as 100%). For this invention, specificity is understood to be a measurement of false positives, where a specificity of 100% means there are no false positives (i.e., no suggestion of the presence of bladder cancer when the patient does not in fact have bladder cancer). Sensitivity is understood to be a measurement of false negatives, where a sensitivity of 100% means there are no false negatives (i.e., no suggestion that there is no bladder cancer when the patient in fact does have bladder cancer).

In another embodiment of this invention, bladder cancer is tested for and its grade evaluated by quantitatively measuring HAase in a sample of biological fluid (such as a urine specimen) collected from a patient suspected of having bladder cancer. As with HA, any conventional assay methodology can be used to determine the presence and measurement of HAase, including radioassays, sandwich assays, inhibition assays and the like. However, HAase is preferably measured by a competitive binding assay. More preferably, the assay of the invention works in the same manner as an ELISA test, but does not make use of antibody completing mechanisms.

For instance, bladder cancer can be detected in an assay method comprising the steps of:

(a) coating a solid support (preferably, microtiter wells) with HA;

(b) contacting and incubating a biological sample collected from a person suspected of having bladder cancer with the coated solid support, under conditions such that the HAase present in the sample (if any is present) is permitted to degrade the HA coated on the solid support;

(c) contacting and incubating HA binding protein (HABP) with the coated solid support, under conditions such that the HABP is permitted to bind to any non-degraded HA coated on the solid support;

(d) determining the amount of HABP bound to the HA coated on the solid support, and determining therefrom the amount of HA present in the sample.

In this embodiment, where HAase is present in the sample, it will degrade the coated HA and permit less HABP to bind to the coated HA, as determined by, for instance, comparison with a standard. A low measurement of HABP bound to the coated HA, then, would be indicative of either intermediate or high grade bladder cancer.

The preferred way to determine the amount of HABP bound to the HA coated on the solid support, and determine therefrom the amount of HAase present in the sample, is to detect a signal associated with or produced by the bound HABP.

For example, a microtiter plate reader can be used to measure absorbance of colored product as an indirect measure of biotinylated HABP bound to the solid support (avidin-enzyme conjugate and labeled substrate are used to generate the colored product). The maximum absorbance can be obtained by incubating the HA-coated wells with buffer alone in the absence of any HAase or HAase-containing sample. A standard graph can be prepared by plotting absorbance versus mU/ml of Streptomyces HAase. Using this standard graph, the HAase concentration (mU/ml) in each dilution of the sample can be calculated. From several such determinations the mean HAase concentration in each sample can be determined. Protein concentration (mg/ml) of the sample can be determined by automated analysis or with a protein assay kit (BioRad, Richmond, Calif.). The HAase concentrations can be normalized to the protein content and expressed as mU/mg protein.

The calculations for determining urinary HAase levels can be as follows: A×dilution factor÷mg/ml urinary protein, where A is mU/ml of HAase concentration as extrapolated from the standard graph. The HAase levels are finally expressed as mU/mg total protein. A low absorbance reading would indicate a high amount of HAase present in the urine sample, which itself would indicate intermediate- or high-grade bladder cancer in the patient.

In general, a calculation of more than about 10 mU/mg HAase is indicative of intermediate or high grade bladder cancer in the patient.

The sensitivity of this method to detect the intermediate- to high-grade bladder cancer can be about 85% or more (and may be as high as 100%) and the specificity can be about 88% or more (and may be as high as 100%).

To detect low-grade bladder cancer, a combination of HA and HAase tests may be used. A calculation of less than about 10 mU/mg HAase (corresponding to a higher amount of HABP bound to the coated HA) is indicative of either low grade bladder cancer or no bladder cancer at all. This embodiment of the invention utilizing an HAase assay does not distinguish between the presence of low grade bladder cancer or no bladder cancer at all. Consequently, it is preferred that the HA assay be used in conjunction with the HAase assay to test a patient, because the HA assay can detect the presence of even low grade bladder tumors, although it does not distinguish between particular grades. Thus, in order to detect and diagnose a low grade bladder tumor, both the HA and the HAase assays should be run. The HA assay would give a positive result (i.e., levels of HA exceeding about 500 ng/mg, indicating the presence of a tumor), while the HAase assay would give a negative result (i.e., levels of HAase less than about 10 mU/mg, indicating that there is no intermediate or high grade tumor present).

In a further embodiment, the invention relates to diagnostic kits for testing and evaluating bladder cancer. The kit comprises HA and/or HAase, HABP and a marker or HABP conjugated to a marker, and ancillary reagents suitable for use in detecting the presence of HA and/or HAase in a biological sample. An example of a diagnostic kit contemplated by this invention is a conventional dipstick test device.

These and other embodiments of the instant invention are described in further detail below.

A: The scatter diagram of individual HA levels. In each category, a dot represents the urinary HA level of each individual and "n" represents the number of individuals tested. GU, represents the category of patients with genito-urinary conditions such as BPH (n=8), prostate cancer (n=7), kidney stones (n=5), cystitis (n=12), urinary tract infections (n=8), prostatitis (n=2), epididymitis (n=1) and renal trauma (n=2). G3 category includes 34 patients with G3 tumor (stages T1–T4) and 9 CIS patients. The dash line represents a minimum cut-off limit of 500 ng/mg HA concentration.

B: The comparison of the mean urinary HA levels among various categories. The mean levels are calculated from the individual HA levels presented in "A". The results represent ng of mean HA levels per mg protein±SEM.

FIGS. 6A and B: Determination of HA levels in bladder tissue extracts. The concentration of HA in tissue extracts was determined by ELISA-like assay as described in EXAMPLE 2 below.

A: The scatter diagram of individual HA levels. In the text, G1 and G2+G3 tumors are referred to as low-grade and high-grade TCCs respectively.

B: HA concentrations (mean±SEM) among normal bladder and TCCs tissue extracts.

Figure 7:
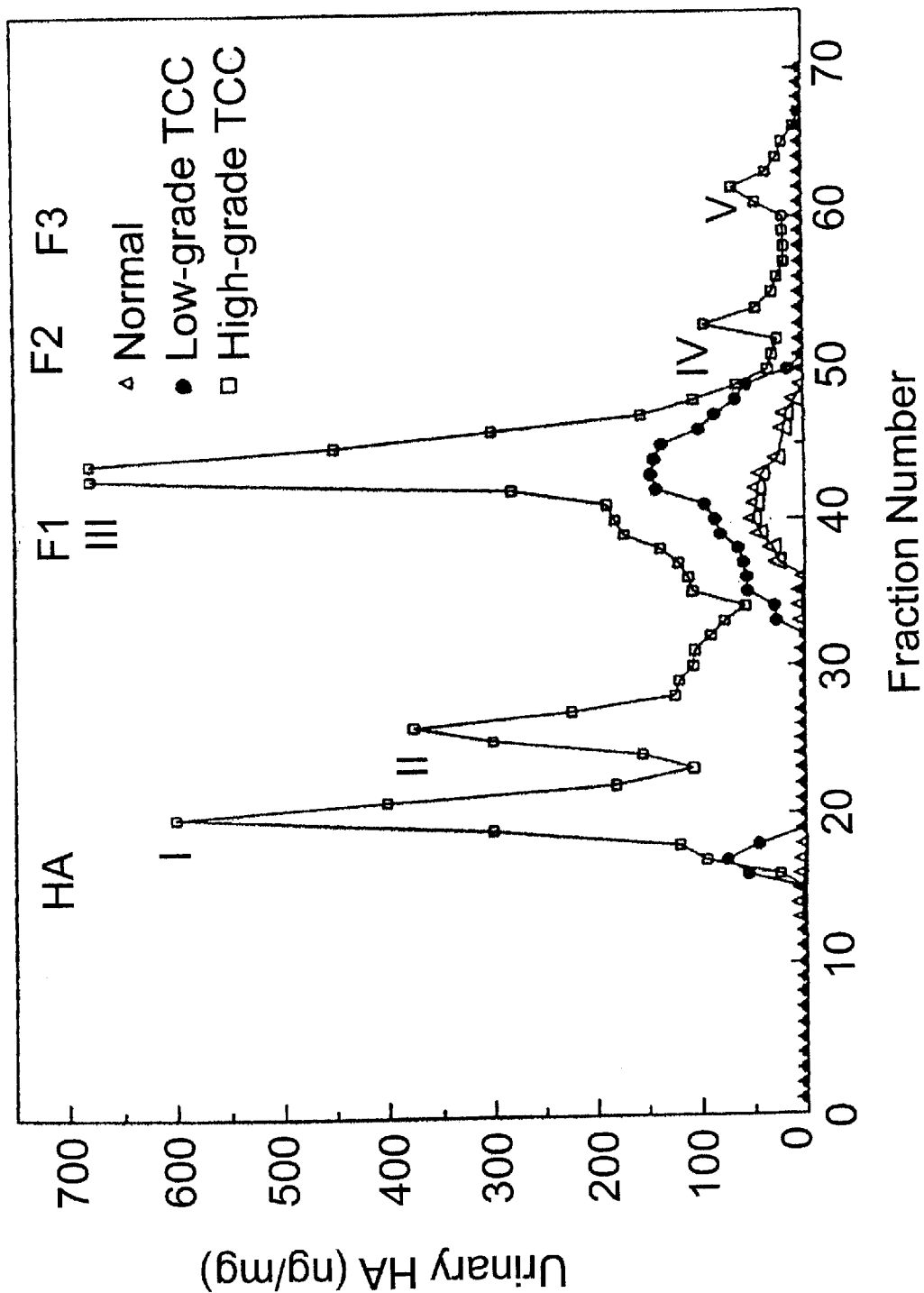

FIG. 7: Examination of the urinary HA profiles of normal individuals and bladder cancer patients. The sizes of HA species present in the urine of normal individuals (n=4) and patients with either low-grade TCCs (G1 tumor, n=4) or high-grade TCCs (n=5, G2, n=2 and G3, n=5) were determined by gel-filtration chromatography, on a Sepharose 6 CL-B column, as described in EXAMPLE 2 below. The column was standardized using high-molecular mass HA (Mr 2×10$^6$ dalton) and HA fragments, F1 (10–15 disaccharide units), F2 (2–3 disaccharide units) and F3 (~2 disaccharide units). I–V represent HA peaks present in the urine of high-grade TCC patients.

FIGS. 8A and B: Effect of HA and HA fragments on HMVEC-L mitogenic response. HMVEC-L cells were incubated with HA or HA fragments in "Endothelial cell basal medium" at 37° C. for 18 h, followed by incubation with [$^3$H]-thymidine for 2 h, as described in EXAMPLE 2 below.

A: Effect of HA or HA fragments, generated in vitro on HMVEC-L mitogenic response. Control represents the incorporation of [$^3$H]-thymidine in DNA, in the absence of any added HA or HA fragments. The [$^3$H]-thymidine (dpm 1031±87) incorporated in control samples is designated as 100%. The results are an average of triplicate determinations.

B: Effect of HA and HA fragments (peaks I–V) isolated from high-grade TCC patients' urine (FIG. 7) on the mitogenic response of HMVEC-L cells. A single concentration (2 μg/ml) of HA present in various peaks was used to test the mitogenic response. Control represents [$^3$H]-thymidine incorporation in the absence of any added HA. The dpm 838±49 incorporated in the control samples are designated as 100%. The results are mean±s.d. of triplicate determinations.

Figure 9:

FIG. 9: Detection of urinary hyaluronidase activity by substrate (HA)-gel assay. Urine specimens (≈20 μg protein) were electrophoresed on a 7.5% SDS-PAGE substrate (HA)-gel under non-denaturing conditions. Following electrophoresis, the gels were incubated in the assay buffer to allow HA digestion, stained and destained as described in EXAMPLE 3 below. Lanes 1 and 2: separate normal subjects; lanes 3 and 4: individual patients with G1 tumor; lanes 5 and 6: individual patients with G3 tumor.

Figure 10:
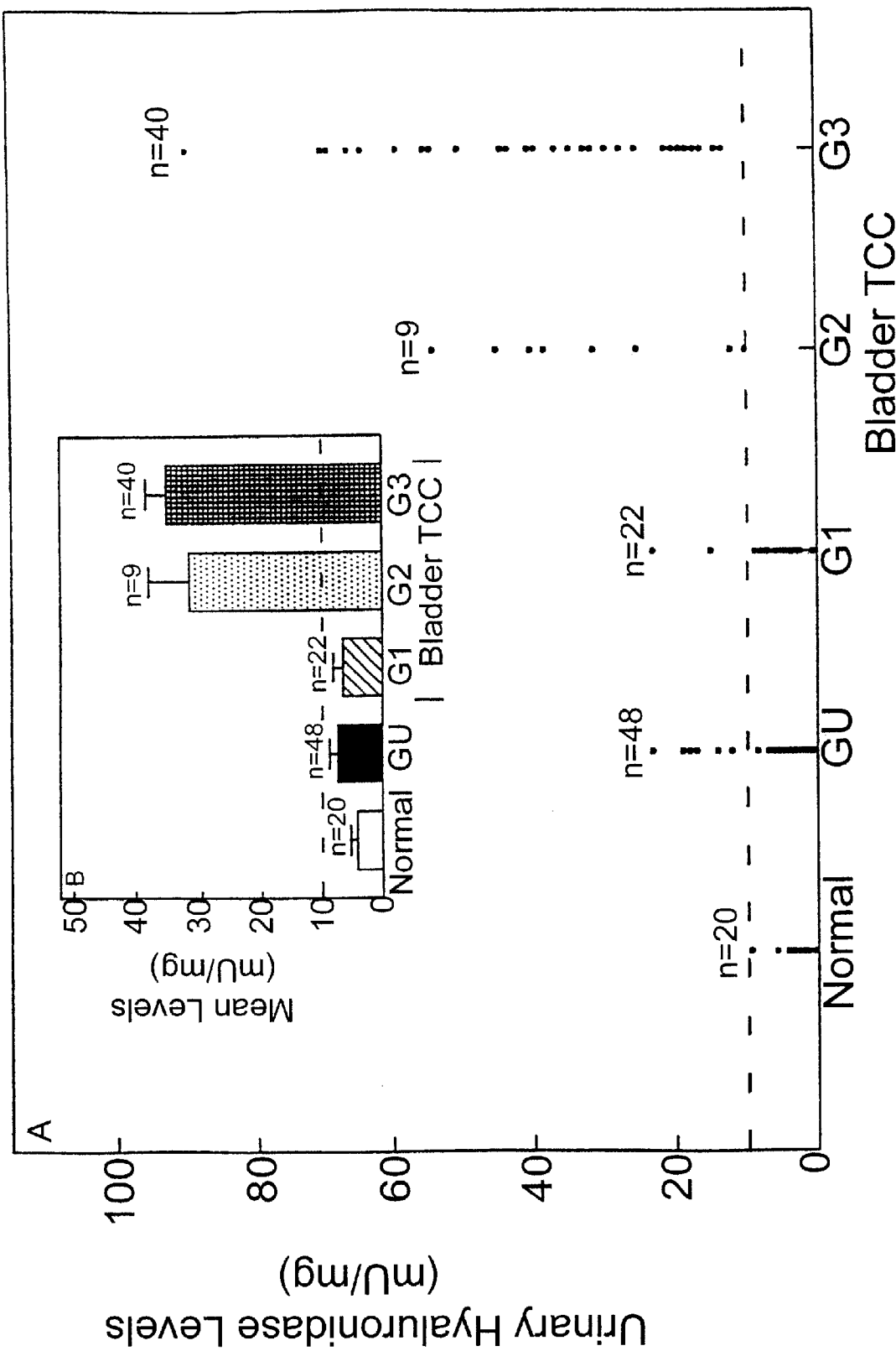

FIGS. 10A and B: Quantitative determination of urinary hyaluronidase activity by an ELISA-like assay. The hyaluronidase activity was measured as described in EXAMPLE 3 below.

A: The scatter diagram of individual hyaluronidase activities. In each category, a dot represents the urinary hyaluronidase activity of each individual and "n" represents the number of individuals tested. GU: This category includes patients with genito-urinary conditions such as advanced prostate cancer (n=10), BPH (n=8), kidney stones (n=5), cystitis (n=12), urinary tract infections (n=8), prostatitis (n=2), epididymitis (n=1), and renal trauma (n=2). G3: The category includes patients with G3 tumors (n=34, stages T1–T4) and CIS (n=6).

B: The comparison of the mean hyaluronidase activity among various categories. The mean activity was calculated from the individual hyaluronidase activities presented in "A". The results represent mU of mean hyaluronidase activity per mg protein±SEM.

Figure 11:
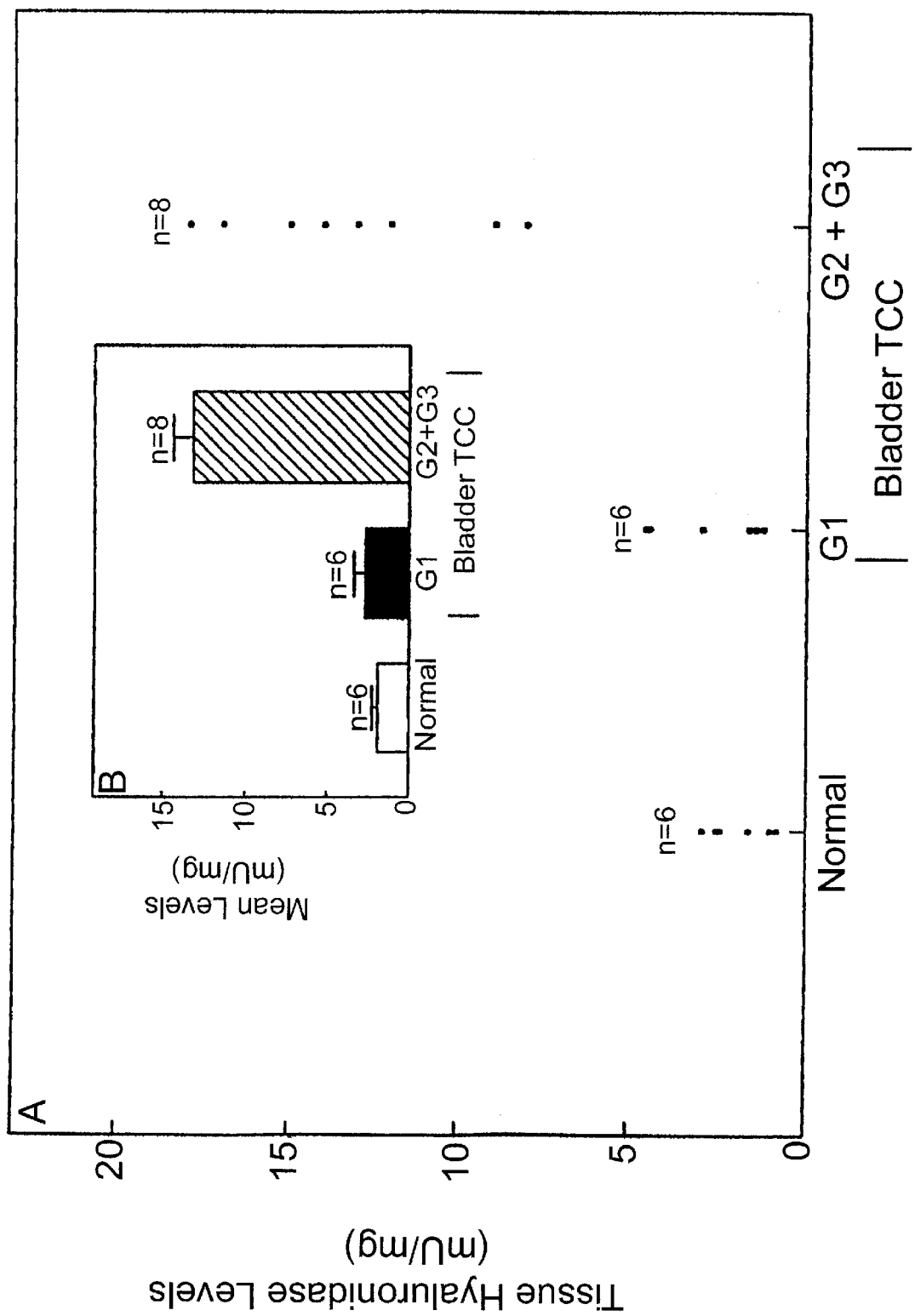

FIGS. 11A and B: Determination of hyaluronidase activity in bladder tissue extracts. The hyaluronidase activity in tissue extracts was determined by the ELISA-like assay as described in EXAMPLE 3 below.

A: The scatter diagram of individual hyaluronidase activities.

B: Hyaluronidase activity (Mean±SEM) among normal and bladder TCC tissue extracts.

Figure 12:
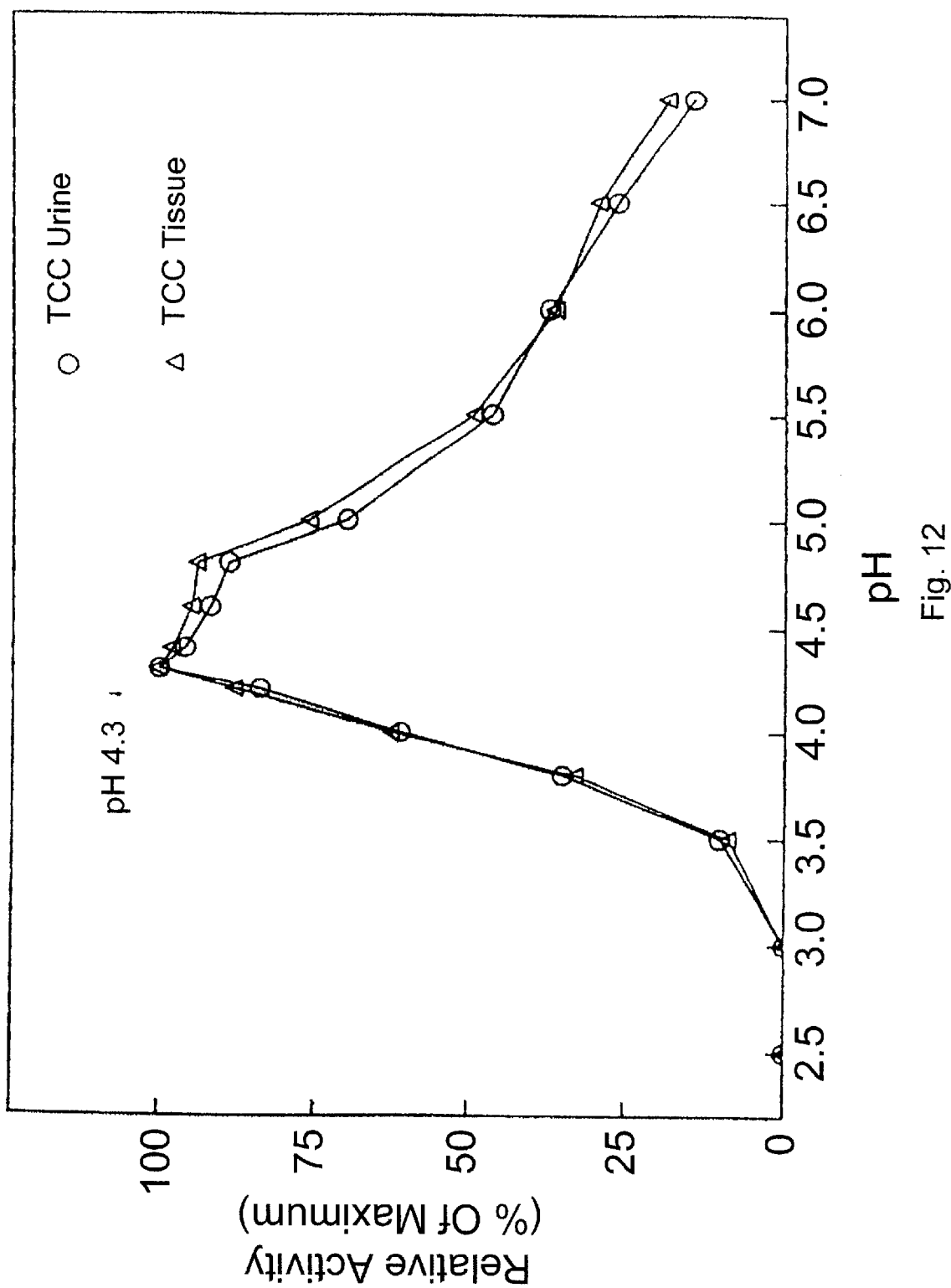

FIG. 12: Determination of the pH activity profile of bladder tumor-associated hyaluronidase. A urine specimen and a tumor tissue extract obtained from a patient with a high-grade bladder tumor were incubated on HA-coated wells at different pH. Following incubation, HA remaining on the wells was estimated as described in EXAMPLE 3 below. The results are calculated as described in EXAMPLE 3 below.

FIGS. 13A, B and C: Molecular mass determination of bladder-tumor derived hyaluronidase by substrate (HA) SDS-PAGE.

A: Substrate (HA) SDS-PAGE analysis of urine specimens. Urine specimens (~40 μg protein) were separated on a 9% SDS-PAGE minigel together with the BioRad broad range prestained molecular weight markers. Following electrophoresis the gel was processed as described in EXAMPLE 3 below. Lane 1: urine specimen from a patient with G1 tumor; lane 2: urine specimen from a patient with G2 tumor; lane 3: urine specimen from a patient with G3 tumor; lane 4: urine specimen from a normal individual.

B: SDS-PAGE analysis of total urinary proteins. Urine specimen (~20 μg protein) from a patient with G3 tumor were separated by 12% SDS-PAGE together with BioRad prestained broad range molecular weight markers. Following electrophoresis, the gel was silver stained.

C: Substrate (HA) SDS-PAGE analysis of tissue extracts. Extracts (40 μg protein) prepared from a G3 tumor and a normal bladder tissue specimens were separated on a 12% substrate (HA) SDS-PAGE together with BioRad prestained broad range molecular weight markers. Following electrophoresis the gel was processed as described in EXAMPLE 3 below. Left lane: G3 tumor tissue extract; right lane: normal bladder tissue extract.

DETAILED DESCRIPTION OF THE PRESENT INVENTION

Prior to this invention, a non-invasive, highly selective and highly specific method for detecting bladder cancer and evaluating its grade has not been known. It has not previously been known that urinary HA levels can be used as markers to detect bladder cancer detection and that urinary hyaluronidase levels are diagnostic indicators of the grade of the bladder tumor. There has been no suggestion that HA and hyaluronidase levels in urine can together be diagnostic in detecting an invasive carcinoma. Furthermore, ELISA-like assays that describe the use of biotinylated HA binding protein (but do not employ antibodies) and the specific techniques described below, have not been used to determine urinary HA and hyaluronidase levels.

Hyaluronic Acid (HA) Determination (HA Test)

As shown below in the examples, the HA assay of the invention, at about 500 ng/mg, shows a sensitivity of about 88% or more (although it may be as high as 100%) to detect bladder tumors and specificity of about 87% or more (although it may be as high as 100%). This represents an advantage and improvement over the presently known methods for detecting bladder cancer.

Of course, as would be appreciated by someone skilled in this art, cut-off limits of HA concentration may vary, and the population spread must be taken into consideration. Setting the cut-off limit of HA concentration to arrive at appropriate determinations of bladder cancer status may involve considering factors such as, for example: age, diet, concentration of protein in the sample, environmental influence, genetic background, hydration status, medical history, physical condition, sex, weight, or the like.

The ability to detect even low-grade and low-stage bladder tumors (i.e., G1 and Ta tumors) using HA assays represents another important feature of this embodiment of the invention. The three known non-invasive urinary tests mentioned above—namely, the hematuria home screening test, the Bard BTA test, and the NMP22 test—do not detect these tumors with high sensitivity. Such tumors also go undetected for a long period of time due to lack of any clinical manifestations. However, as discussed below, urinary HA levels detect low-grade and low-stage (88–90%), as well as high-grade and high-stage tumors (88–96%), with similarly high sensitivities.

As mentioned above, any conventional assay system can be employed with the invention to detect bladder cancer, as long as it measures levels of HA in the biological fluid sample. The assays of this invention, both HA and HAase, are not limited to urine, but also may be used to test biological fluids such as blood, serum, plasma, ascitic fluid, peritoneal fluid, bile, seminal fluid and cerebrospinal fluid.

In the preferred embodiment of the HA assay, the method of the invention starts with adsorbing HA onto the surface of a solid phase. The HA can be derived from any convenient source, such as human umbilical cord. The solid phase can be any conventional solid phase, including nitrocellulose and the like, and preferably microtiter wells. After adsorbing HA onto the solid phase, the surface of the solid phase is preferably washed using conventional buffer(s).

Because the solid phase still has sites left on its surface which are capable of coupling with the HA or other molecules, it is preferred that prior to addition of the sample a blocking substance be added so as to cover any part of the solid phase on which the HA has not been adsorbed. Examples of suitable blocking substances include γ-globulin and albumin derived from cows or other animals. Bovine serum albumin is preferred. After blocking the free sites of the solid phase, the surface of the solid phase is preferably washed using conventional buffer(s).

Next, since HA is the analyte of interest, HA binding protein (HABP) is added to the coated solid support in the presence of a sample of biological fluid collected from a person suspected of having bladder cancer, and incubated under conditions such that the HABP is permitted to bind to the HA coated on the solid support and the urinary HA (if any is present). The incubation time and conditions can vary within wide limits, but an incubation time of about 4 to about 16 hours, and an incubation temperature of about 4° C. to about 37° C. is satisfactory. Longer or shorter incubation times and higher or lower incubation temperatures are also possible, as would be understood by someone of ordinary skill in this art.

HABP suitable for use with the assays of this invention can be readily purified from a number of sources, such as bovine nasal cartilage (Tengblad, Biochim. Biophys. Acta, 578: 281–289, 1979), pig laryngal cartilage (Fosang et al., Matrix, 10: 306–313, 1990).

After binding of the HABP to the coated HA and/or the sample HA, the surface of the solid phase is preferably washed using conventional buffer(s).

Next, the amount of HABP bound to the HA coated on the solid support is determined. Preferably, the HABP is biotinylated, and the bound HABP is visualized following incubation with an avidin-enzyme conjugate and any substrate for the enzyme which generates a colored product. Such a detection system does not use radioactivity as a label, multiple markers (i.e., enzyme molecules) are immobilized for every HABP bound to the solid support, and the signal (i.e., colored product) is amplified through turnover of the enzyme. However, any conventional marker system may be used in conjunction with the HABP. Examples of suitable marker systems include enzymes, fluorescence, chemiluminescence, enzyme-substrate, isotope markers, radiolabels and the like. Preferably, the determination of the amount of HABP bound to the HA coated on the solid support is via an avidin-biotin detection system. Another useful marker system employs keratin sulfate and keratin sulfate-reactive antibodies. The urinary HA levels can usefully be determined using a microtiter plate reader, and can be extrapolated from a standard graph. The amount of HABP coupled with the coated HA can then be correlated with the existence of bladder cancer in the patient from whom the sample of biological fluid was collected.

For the HA assay, purified hyaluronic acid is preferably used as a standard.

Hyaluronidase (HAase) Determination (HAase Test)

In this invention, where HAase is the analyte of interest, HA is adsorbed onto the surface of a solid phase in the same fashion as described above for the HA assay. Any conventional assay system can be employed with the invention to detect bladder cancer, as long as it measures levels of HAase in the sample of biological fluid.

After adsorbing HA onto the solid phase, the surface of the solid phase is preferably washed using conventional buffer(s).

Next, a sample of biological fluid (e.g., urine) collected from a person suspected of having bladder cancer is added to the coated solid support, and incubated under conditions such that the HAase present in the sample (if any is present) is permitted to degrade the HA coated on the solid support.

Following incubation, the degraded HA is preferably removed by washing using conventional buffer(s).

Next, it is preferred that prior to addition of HABP, a blocking substance (e.g., serum albumin) be added so as to cover any part of the solid phase on which the HA has not been adsorbed, as described above for the HA assay. After blocking the free sites of the solid phase, the surface of the solid phase is preferably washed using conventional buffer(s).

Then, the solid phase is exposed to HABP, under conditions such that the HABP is permitted to bind to any non-degraded HA coated on the solid support. As with the HA assay, the incubation time and conditions can vary within wide limits, but an incubation time of about 30 minutes to about one hour, and an incubation temperature of about 37° C. is satisfactory. Longer or shorter incubation times and higher or lower incubation temperatures are also possible, as would be understood by someone of ordinary skill in this art.

After coupling of the HABP to the coated HA, the surface of the solid phase is preferably washed using conventional buffer(s).

Next, the amount of HABP bound to the HA coated on the solid support is determined. Preferably, the HABP is biotinylated, and the bound HABP is visualized following incubation with an avidin-enzyme conjugate and any substrate for the enzyme that generates a colored product. Such a detection system does not use radioactivity as a label, multiple markers (i.e., enzyme molecules) are immobilized for every HABP bound to the solid support, and the signal (i.e., colored product) is amplified through turnover of the enzyme. However, any conventional marker system may be used in conjunction with the HABP. Examples of suitable marker systems include enzymes, fluorescence, chemiluminescence, enzyme-substrate, isotope markers, radiolabels and the like. Preferably, the determination of the amount of HABP bound to the HA coated on the solid support is via an avidin-biotin detection system. Another useful marker system employs keratin sulfate and keratin sulfate-reactive antibodies. The urinary HA levels can usefully be determined using a microtiter plate reader, and can be extrapolated from a standard graph. The amount of HABP coupled with the coated HA can then be correlated with the existence of bladder cancer and the grade of the cancer in the patient from whom the sample of biological fluid was collected. A calculation of more than about 10 mU/mg is indicative of intermediate or high grade bladder cancer.

Of course, as would be appreciated by someone skilled in this art, cut-off limits of HAase concentration may vary, and the population spread must be taken into consideration. Setting the cut-off limit of HAase concentration to arrive at appropriate determinations of bladder cancer status may involve considering factors such as, for example: age, diet, environmental influences, hydration, physical condition, sex, weight, or the like.

For the HAase assay, purified hyaluronidase is preferably used as a standard.

As shown below in the examples, the sensitivity of the HAase method to detect the intermediate- to high-grade TCCs is about 85% or more (although it may be as high as 100%) and the specificity is about 88% or more (although it may be as high as 100%). Thus, the HAase assay of the invention is useful both to detect intermediate and high grade bladder tumors and to evaluate their grade.

The HA and HAase assays of the invention can be used separately or, preferably, in conjunction with each other. The HAase assay alone does not positively detect and/or evaluate low grade bladder cancers (i.e., calculation of less than about 10 mU/mg). However, as described above, low grade bladder cancer can be detected when both the HA and HAase assays are used to test a patient's biological fluid sample.

Preliminary stability studies show that both the HA and HAase are stable after incubation at room temperature for >8 h (up to about 16 h). The inventors have analyzed the spot urine specimens, and consequently it is established that special conditions such as first morning void are not required. Since the tests of the invention include normalization of the HA (ng/ml) and HAase (mU/ml) levels in the sample to the protein concentration (mg/ml), hydration status of the patient does not influence the result. The normalization to total protein rather than to total creatinine is preferred because the former is less influenced by hematuria, a condition commonly found in bladder cancer patients.

Besides the above-described uses, the assays for HA and HAase of this invention have numerous applications. For instance, as described above, the invention covers methods for screening individuals to detect bladder cancer and evaluating its grade. This is particularly useful to detect early onset of bladder cancer, especially for those who are at a high risk (e.g., smokers, and workers in paint, dye and leather industries).

The invention also contemplates methods to evaluate the efficacy of treatment for bladder cancer (i.e., by testing the patient pre- and post-treatment. Similarly, the invention is useful as a method for long-term follow-up of bladder cancer patients to monitor tumor recurrence.

Further, the assays of the invention are useful to screen, evaluate treatment efficacy and follow-up of all other urological malignancies (i.e., Wilms' tumor, prostate tumors, kidney cancer, ureteral cancer, urethral cancer, renal-pelvic cancer, etc.) where the tumor comes in contact with urine.

The assays are useful to screen other tumors where the tumor comes in contact with any body fluids or normal saline which may be squirted into the tumor to solubilize HA and HAase. The HA and/or HAase can then be assayed.

The invention contemplates any dipstick test applications using HA and/or HAase to detect bladder and/or other urological cancers and evaluate their grade. For example, using conventional methodology a solid phase in the form of a dipstick can be used to assay either HA or HAase, as described above. For instance, as someone skilled in this art would be aware, the dipstick can be coated or impregnated with HA. Of course, the dipstick may be used to test any biological fluid, including but not limited to urine.

All books, articles, and patents cited in this specification are incorporated herein by reference in their entirety. In particular, the present invention was disclosed in U.S. Provisional Appln. No. 60/010,976, filed Feb. 1, 1996, the entire contents of which are hereby incorporated by reference and relied upon.

The following illustrative and comparative examples describe the instant invention in more detail. However, they are not intended to limit the scope of the specification and the claims.

EXAMPLES

Example 1

Initial Study of HA and HAase

Urinary HA and HAase levels were compared among TCCs patients, patients with other GU conditions and normal individuals. The utility of HA and HAase level determinations to assess the treatment efficacy was also evaluated. Two very similar ELISA-like assays involving the use of a biotinylated bovine nasal cartilage HA binding protein (HABP) were employed to measure urinary HA and HAase levels. Urinary HA and HAase levels were normalized to urinary protein levels and expressed as ng/mg protein and mU/mg protein respectively.

Unlike the known assays (such as Stern et al.), in this assay the urinary HA and HAase levels were normalized to urinary protein concentrations to correct for the hydration status of the patient, a significant factor that affects the correlation between urinary HA/HAase levels and bladder cancer/intermediate to high-grade bladder cancer. This is because hydration status is known to affect chemical levels in the urine. Consequently, the normalization of urinary HA/HAase to protein rather than creatinine was preferred because the former is less influenced by hematuria (blood in the urine), a common finding in bladder cancer.

Specimen Collection

Voided urine samples (clean-catch) were collected from all subjects and stored at −20° C. until assayed. At the time of assay, the samples were thawed and centrifuged at 4° C. for 10 min at 2,000 rpm to remove sediments.

Assay For Urinary HA Determination 96-well microtiter wells (Corning, Corning, N.Y.) were coated with human umbilical cord HA (Sigma Chemical Co., St. Louis, Mo.; 25 µg/ml) dissolved in 0.1 M sodium bicarbonate solution, pH 9.2. The coating was performed at 4° C. for ≈16 h (overnight). (This reaction was also run quite successfully at 37° C. for 4 h.)

The HA-coated wells were washed 3 times in phosphate buffered saline (PBS). The non-specific sites on the wells were blocked by incubating the wells in 1% bovine serum albumin (BSA) solution prepared in PBS containing 0.05% Tween 20 (PBS+Tween), at 37° C. for 1 h.

Following incubation, the wells were washed three times in PBS+Tween and then incubated with 200 µl (final volume) (although different volumes can be used, as would be understood by someone skilled in this art) of PBS+Tween containing biotinylated bovine nasal cartilage HA-binding protein (HABP; 1 µg/ml) and several concentrations of urine specimens (0.5–10 µl) or human umbilical cord HA (0.1–60 ng/well or 0.2 ml) at room temperature for 16 h (overnight). HABP was purified according to the method described by Tengblad (Tengblad, Affinity chromatography on immobilized hyaluronate and its application to the isolation of hyaluronate binding proteins from cartilage. Biochim. Biophys. Acta, 578: 281–289, 1979).

Following incubation with HABP the wells were washed five times in PBS+Tween and incubated with PBS plus 0.1% Tween 20 and reagents A and B from an Elite Vectastain ABC kit™ (Vector Laboratories, Burlingame, Calif.) (4 drops of reagents A and B per 10 ml of PBS plus 0.1% Tween 20 solution) at room temperature (≈23° C.) for 30 min as per manufacturers instructions.

Following incubation, the wells were washed three times in PBS+Tween, twice in PBS and incubated with ABTS (2, 2' azino-bis(3-ethyl-benzthiazolin-6-sulfonic acid)) substrate (Vector Laboratories, Burlingame, Calif.) solution prepared by mixing 4 drops each of buffer pH 5.3, ABTS and hydrogen peroxide solutions in 10 ml distilled water as per manufacturers instructions. The microtiter plate was incubated at room temperature in darkness until the color (green) develops.

Figure 3:
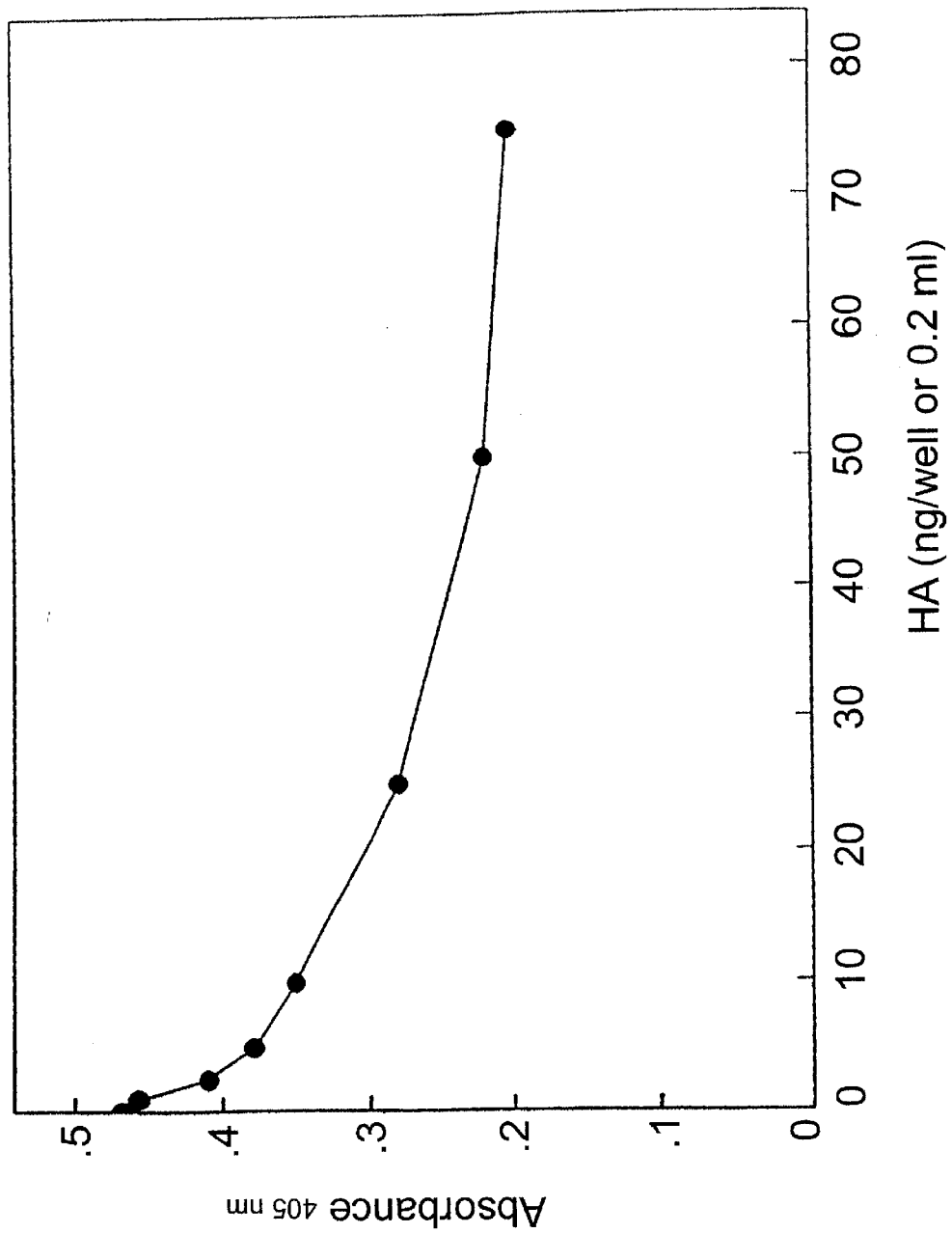
FIG. 3: An example of a typical standard graph for HA ELISA-like assay. The dilutions of urine specimens which yield an absorbance reading in the linear range of the graph are chosen for calculations. HA used to prepare the standard graph is from the human umbilical cord.

The absorbance of the colored product was measured at 405 nm using a microtiter plate reader. In each assay, the maximum absorbance $(A_{max})_{405\ nm}$ was obtained by incubating the HA-coated wells with buffer alone in the absence of any HA or HA-containing urine specimen. $(A_{min})_{405\ nm}$ was obtained by incubation of HA on uncoated wells. A standard graph was prepared by plotting absorbance (405 nm) versus known concentrations of HA (ng/well) used in the assay. An example of a standard graph for this ELISA-like assay is shown in FIG. 3. Using this standard graph, the HA concentration (ng/ml) in each dilution of the urine specimen was calculated. From several such determinations the mean HA concentration in each specimen was determined. Urinary protein concentration (mg/ml) was determined by automated analysis or with a protein assay kit (BioRad, Richmond, Calif.). The HA concentrations were normalized to the protein content and expressed as ng/mg protein. The calculations for determining urinary HA levels were as follows: A×dilution factor÷mg/ml urinary protein, where A is ng/ml of HA concentration extrapolated from the standard graph. An example of a standard graph obtained using human umbilical cord HA is shown in FIG. 3.

Urinary HA Determination

Urinary HA levels were determined in a total of 139 patients. These included normal individuals (n=25), patients with GU conditions (e.g., cystitis, kidney stones, benign prostatic hyperplasia (BPH), urinary tract infections, prostatitis, and renal trauma; n=40) and bladder TCCs patients (n=74; G1, n=17; G2, n=14 and G3+CIS, n=43). As shown in Table 1, the mean urinary HA levels in all TCC patients are 4–7 fold higher than those in normal individuals and patients with various GU conditions (P<0.001).

It is important to note that urinary HA levels are also elevated in a statistically significant manner in patients with low-grade and low-stage (G1, Ta) bladder tumors.

Figure 1:
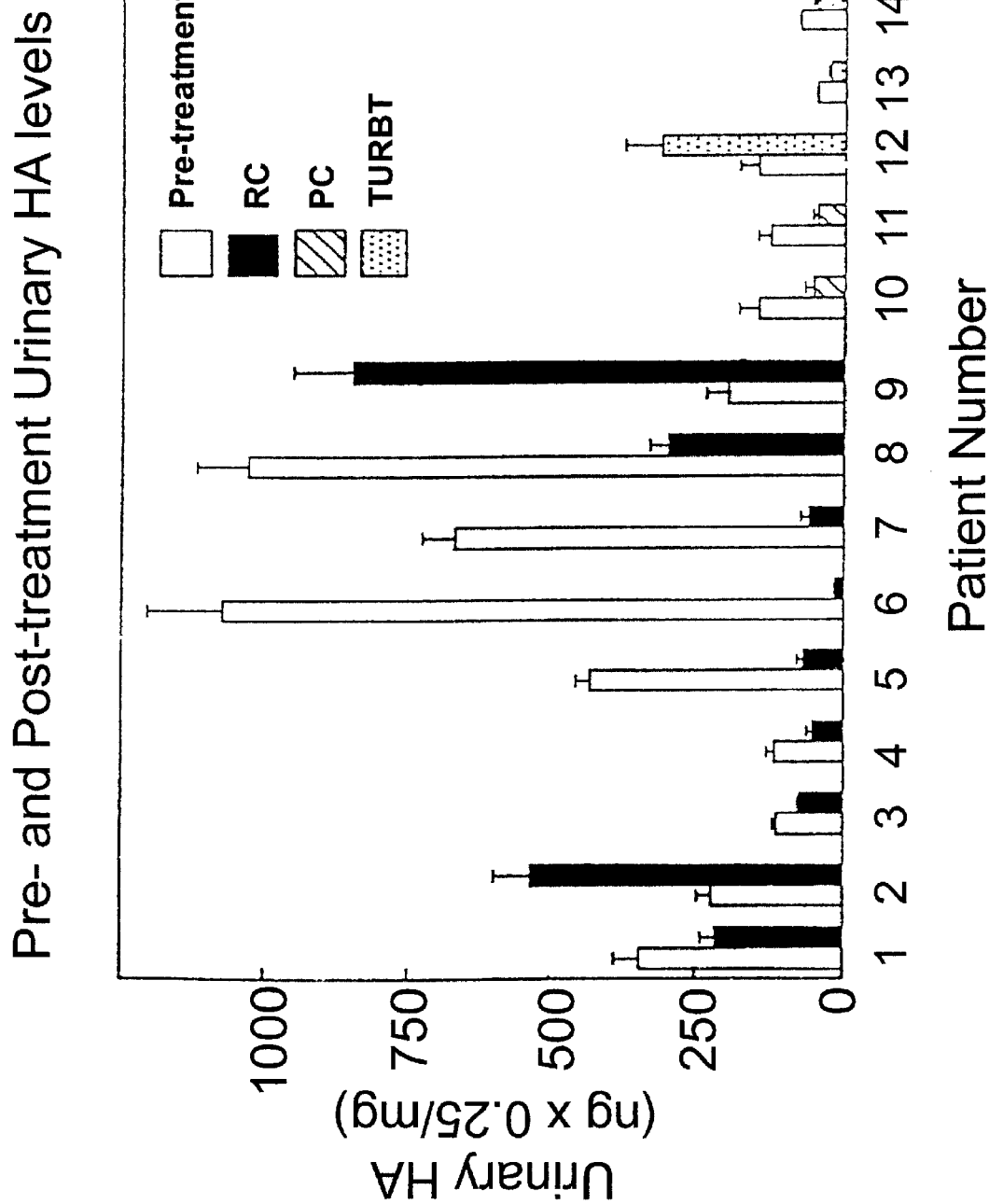
FIG. 1: Determination of treatment efficacy for bladder cancer by determining pre- and post-operative urinary HA levels. Urinary HA levels are expressed as ng/mg protein (Mean±SEM). RC: radical cystectomy; PC: partial cystectomy; TURBT: Transurethral resection of bladder tumor; IC: intravesical chemotherapy. Following RC, patient number 2 and patient number 9 received a neo-bladder and an ileal conduit, respectively. The intestinal mucosa used to make ileal conduit and neobladder may have caused this increase, as intestinal mucosa is rich in glycosaminoglycans, including HA. However, the HAase levels of these two patients showed a ≈5 fold decrease (See FIG. 2: Patient numbers 1 and 7). Therefore, a combination of two methods is more useful to monitor the treatment efficacy.

To evaluate the utility of urinary HA level determinations to monitor treatment efficacy, the pre- and post-treatment urinary HA levels were determined in 14 patients. Post-treatment levels were measured 1–3 weeks following the treatment. As shown in FIG. 1, the pre-operative elevated HA levels show a decrease in the majority of patients following treatment suggesting that urinary HA level determinations are also useful in monitoring treatment efficacy.

Table 1

Determination of urinary HA levels in various groups of individuals by ELISA-like assay. Results are expressed as mean±SEM and "n" represents number of individuals in each category.

TABLE 1

| Category | n | HA levels (ng/mg) |
|---|---|---|
| Normal | 25 | 244.5 ± 32.5 |
| GU patients | 40 | 392.5 ± 37 |
| G1 TCCs | 17 | 1266 ± 210.5 |
| G2 TCCs | 14 | 1456.5 ± 342 |
| G3 + CIS | 43 | 2141.5 ± 335.5 |

Assay For Urinary HAase Determination 96-well microtiter wells (Corning, Corning, N.Y) were coated with human umbilical cord HA (Sigma Chemical Co. St. Louis, Mo.; 200 µg/ml) dissolved in 0.1 M sodium bicarbonate solution, pH 9.2. The coating was performed at 4° C. for ≈16 h (overnight). (This reaction was also run quite successfully at 37° C. for 4 h.)

The HA-coated wells were washed 3 times in phosphate buffered saline (PBS) and incubated with several concentrations of urine specimens (0.5–10 µl) or purified Streptomyces hyaluronidase (0.02–40 mU/ml) (Calbiochem, San Diego, Calif.) in 100 µl (although different volumes can be used, as would be appreciated by someone skilled in this art) of HAase-ELISA buffer (0.1 M sodium formate, 0.1–0.15 M NaCl and 0.2 mg/ml bovine serum albumin (BSA), pH 4.3), at 37° C. for ≈16 h (overnight).

Following incubation, the degraded HA on the wells was removed by washing the wells in a solution containing PBS and 0.05% Tween 20 (PBS+Tween). The non-specific sites on the wells were blocked by incubating the wells in 1% BSA solution prepared in PBS+Tween, at 37° C. for 1 h.

Following incubation the wells were washed three times in PBS+Tween and incubated in a solution containing PBS+ Tween, 0.1% BSA and 5 µg/ml of biotinylated bovine nasal cartilage HA-binding protein (HABP) at 37° C. for 1 h. HABP was purified according to the method described by Tengblad (Tengblad, Affinity chromatography on immobilized hyaluronate and its application to the isolation of hyaluroate binding proteins from cartilage. Biochim. Biophys. Acta, 578: 281–289, 1979).

Following incubation with HABP, the wells were washed five times in PBS+Tween and incubated with PBS plus 0.1% Tween 20 and reagents A and B from an Elite Vectastain ABC kit™ (Vector Laboratories, Burlingame, Calif.) (4 drops of reagents A and B per 10 ml of PBS plus 0.1% Tween 20 solution) at room temperature (≈23° C.) for 30 min as per manufacturers instructions.

Following incubation, the wells were washed three times in PBS+Tween, twice in PBS and incubated with ABTS (2, 2' azino-bis(3-ethyl-benzthiazolin-6-sulfonic acid)) substrate (Vector Laboratories, Burlingame, Calif.) solution prepared by mixing 4 drops each of buffer pH 5.3, ABTS and hydrogen peroxide solutions in 10 ml distilled water as per manufacturers instructions. The microtiter plate was incubated at room temperature in darkness until the color (green) develops. The absorbance of the colored product was measured at 405 nm in a microtiter plate reader.

Figure 4:
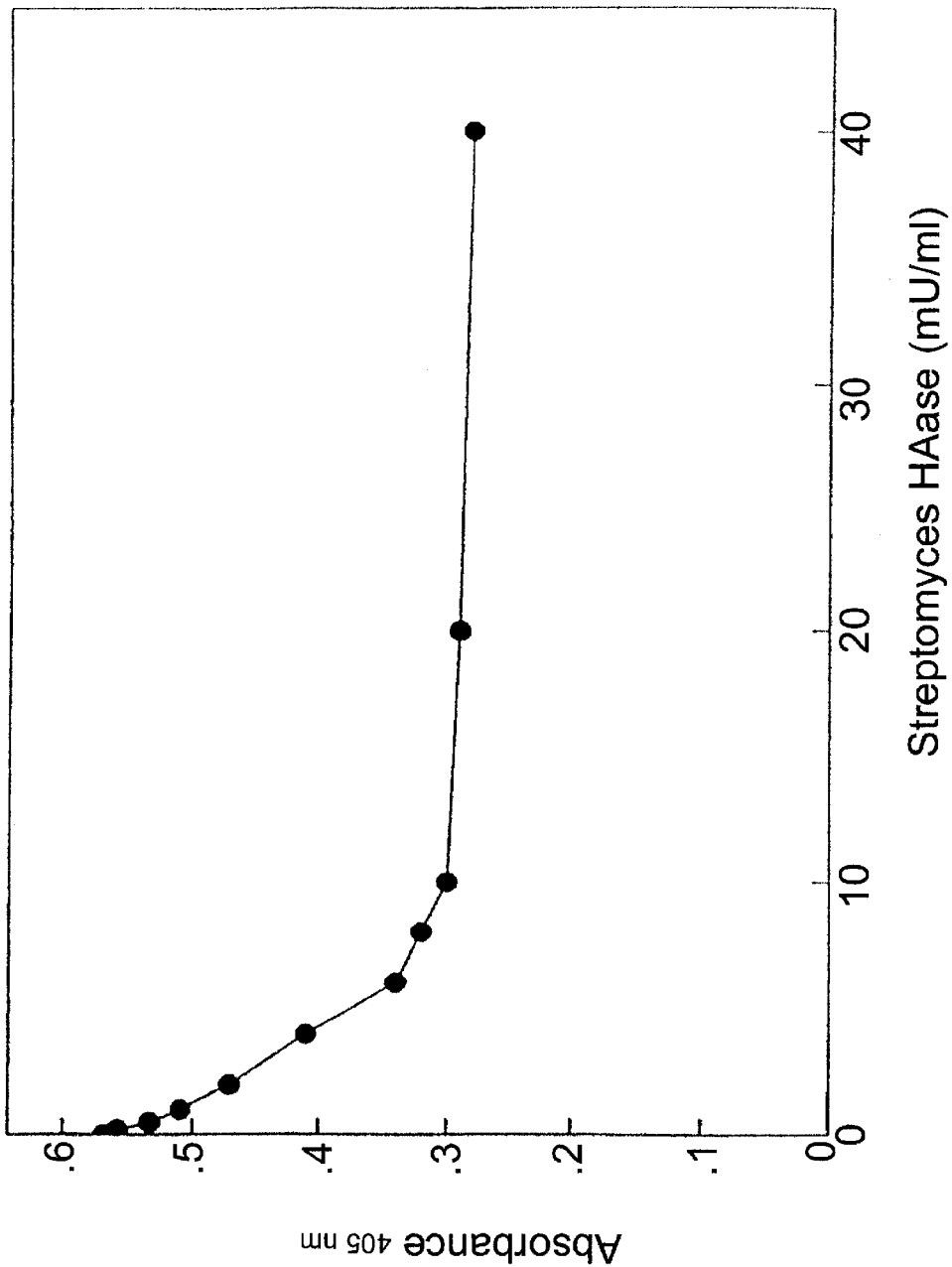
FIG. 4: An example of a typical standard graph for HAase ELISA-like assay. The dilutions of urine specimens which yield a absorbance reading in the linear range of the graph are chosen for calculations. HAase used to prepare the standard graph is from the Streptomyces sp.

In each assay, the maximum absorbance ($A_{max}$) $_{405\,nm}$ was obtained by incubating the HA-coated wells with buffer alone in the absence of any HAase or HAase-containing urine specimen. ($A_{min}$) $_{405\,nm}$ was obtained by incubation of HAase on uncoated wells. A standard graph was prepared by plotting absorbance (405 nm) versus known concentrations of Streptomyces HAase (mU/ml). An example of a standard graph for this ELISA-like assay is shown in FIG. 4. Using this standard graph, the HAase concentration (mU/ml) in each dilution of the urine specimen was calculated. From several such determinations the mean HAase concentration in each urine specimen was determined. Urinary protein concentration (mg/ml) was determined by automated analysis or with a protein assay kit (BioRad, Richmond, Calif.). The HAase concentrations were normalized to the protein content and expressed as mU/mg protein.

The calculations for determining urinary HAase levels were as follows: A×dilution factor÷mg/ml urinary protein, where A is mU/ml of HAase concentration as extrapolated from the standard graph. An example of the standard graph obtained using Streptomyces HAase is shown in FIG. 4.

Urinary HAase Determination

Urinary HAase levels were examined in a total of 131 patients. These included normal individuals (n=16), patients with GU conditions (n=45; patients with benign conditions described above (n=35) and patients with advanced prostate cancer, n=10) and bladder TCC patients (n=70; G1, 22; G2, 9 and G3+CIS, 39).

As shown in Table 2, the urinary HAase levels in patients with either G2 or G3 +CIS tumors are 5–8 fold higher than those in patients with G1 tumors, patients with GU conditions and normal individuals (P<0.001). The ELISA-like assay, at 10 mU/mg cut-off limit, has a sensitivity of 100% and a specificity of 88% to detect intermediate- to high-grade TCCs.

Figure 2:
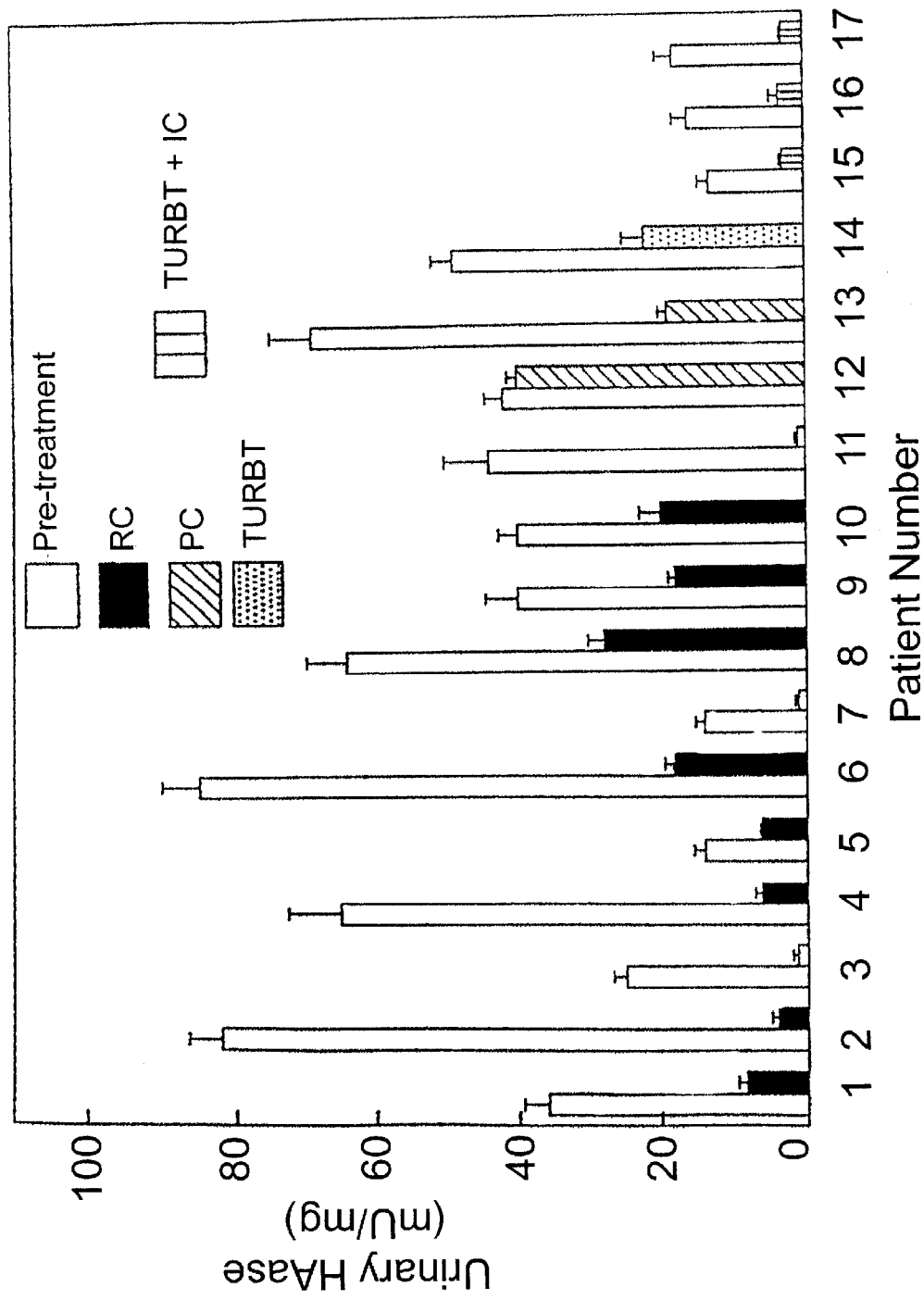
FIG. 2: Determination of treatment efficacy for high-grade bladder cancer by determining pre- and post-operative urinary HAase levels. Urinary HAase levels are expressed as mU/mg protein (mean±SEM). The abbreviations used are the same as described in FIG. 1 legend.

To evaluate the utility of urinary HAase levels to monitor treatment efficacy, pre- and post-treatment HAase levels were measured in 17 patients with high-grade TCCs (G3 tumor or CIS). As shown in FIG. 2, the pre-operative urinary hyaluronidase levels show a decrease in the majority of patients following treatment showing that measurement of urinary HAase levels is useful in monitoring treatment efficacy.

Table 2

Determination of urinary HAase levels in various groups of patients by ELISA-like assay. The results are expressed as mean±SEM and "n" represents number of individuals in each category.

TABLE 2

| Category | n | HAase levels (mU/mg) |
|---|---|---|
| Normal | 16 | 4.3 ± 1.2 |
| GU patients | 45 | 7.4 ± 1.4 |
| G1 TCCs | 22 | 6.5 ± 1.7 |
| G2 TCCs | 9 | 32 ± 6.1 |
| G3 + CIS | 39 | 34.3 ± 3.1 |

Example 2

Updated Studies and Data of Example 1

Hyaluronic Acid Determination

Urine Specimens

Voided (clean-catch) urine specimens were collected from 144 individuals under a protocol approved by the Institutional Review Board of University of Miami. The samples were divided into three groups. Group 1: normal (healthy) age-matched (30–70 yr) individuals (n=25). Group 2: patients with other genito-urinary conditions (n=45), such as benign prostate hyperplasia (BPH; n=8), prostate cancer (n=7); kidney stones (n=5), cystitis (n=12), urinary tract infections (n=8), prostatitis (n=2), epididymitis (n=1) and renal trauma (n=2). Group 3: bladder cancer patients with G1 (n=17, stage Ta), G2 (n=14, stages Ta–T2) or G3 (n=43) tumors. The G3 subcategory of bladder cancer patients included 34 individuals with G3 tumor (stages T1–T4) and 9 with carcinoma in situ (CIS). CIS is a sub-class of high-grade bladder tumors that are flat and superficial (confined to the urothelium). All specimens were collected and stored at −20° C. until assayed.

Tissue Specimens

Normal bladder tissues from adults (21–50 years) were obtained from organ donors according to relevant state and federal regulations. Neoplastic bladder tissues were obtained from patients (41–72 years) undergoing cystectomy or transurethral resection of the bladder tumor. Group 1: normal adult bladder tissues (n=6). Group 2: low-grade TCC (G1 tumor; n=6). Group 3: high-grade TCC (G2 n=2 and G3, n=6 tumors). To evaluate the grade, each tumor specimen was split and the mirror image segment was fixed in formalin, embedded in paraffin, sectioned and analyzed histologically.

Tissue Extracts

Tissue specimens (≈0.5–1 g) were homogenized in 5 mM HEPES buffer pH 7.2, containing 1 mM benzamidine-HCl. The homogenates were clarified by centrifugation at 40,000×g for 30 min and the clear extracts were assayed.

ELISA-like Assay for HA Level Determination

The concentration of HA in urine specimens and tissue extracts was determined by an ELISA-like assay described by Fosang et al. (An ELISA plate based assay for hyaluronan using biotinylated proteoglycan G1 domain (HA-binding) region. Matrix, 10: 306–313, 1990) with the following modifications.

96-well microtiter plates coated with human umbilical cord HA (25 $\mu$g/ml) were incubated with serial dilutions of urine specimens, tissue extracts or human umbilical cord HA (Sigma Chemical Co., St. Louis, Mo.), in phosphate buffer saline (PBS) +0.05% Tween 20 (PBS+Tween), and a biotinylated bovine nasal cartilage HA-binding protein (1 $\mu$g/ml). Following incubation at room temperature for 16 h, the wells were washed in PBS+Tween. The HA-binding protein bound to these wells was quantitated using an avidin-biotin detection system and ABTS (2,2' azino-bis(3-ethyl-benzthiazolin-6-sulfonic acid)) substrate (Vector Laboratories, Burlingame, Calif.). A standard graph was prepared by plotting absorbance (405 nm) versus human umbilical cord HA concentrations (ng/ml). Using this graph, the HA concentration in each dilution of either the urine specimen or tissue extract was calculated. From several such determinations, the mean HA concentration in each sample was determined and then normalized to the protein concentration (mg/ml) in the sample, where the sample could be urine or a tissue extract. The total protein concentration in each clinical sample was determined with a protein detection kit (BioRad, Richmond, Calif.).

Preparation of HA Fragments

Human umbilical cord HA (~500 mg) was digested with 20,000 units of testicular hyaluronidase (Sigma Chemical Co., St. Louis, Mo.), at 37° C. for different time intervals. The HA fragments generated were separated on a Sephadex G-50 column (1.5×120 cm). Ten ml fractions were collected and assayed for the uronic acid content (Bitter and Müir, A modified uronic acid carbazole reaction. Anal. Biochem., 4: 330–334, 1962). The fractions were combined to give three preparations, F1, F2 and F3. The number of reducing ends in each fraction was determined by the Dygert assay (Dygert et al., Determination of reducing sugars with improved precision. Anal. Biochem., 13: 367–374, 1965). Since each linear polysaccharide of HA or its fragment contains a single reducing end, the chain length of each fragment was calculated from the number of reducing ends per mole of uronic acid. The size range of oligosaccharides in each fraction was also determined by incorporating $^3$H-labeled HA (prepared as described in Lokeshwar et al., Ankyrin binding domain of CD44(GP85) is required for the expression of hyaluronic acid-mediated adhesion function. J. Cell Biol., 126: 1099–1109, 1994) during HA digestion and analyzing the fragments by gel electrophoresis and flurography.

Isolation of HA and HA Fragments from Patient Urine

Urine specimens from normal subjects (n=4) and patients with low-grade TCC (G1 tumor, n=4) or high-grade TCC (G2, n=2 and G3, n=3, tumors) were concentrated 10-fold and dialyzed extensively against PBS. Approximately 2 ml of each of the dialyzed specimens (~20 mg protein) was applied to a Sepharose 6 CL-B column (1.5×120 cm) (Pharmacia, Piscataway, N.J.) equilibrated with PBS. The column was run in PBS at 7 ml/hr and 3.5 ml fractions were collected. The fractions were assayed for HA by the ELISA-like assay as described above. Since the standard globular protein markers and linear polysaccharides such as HA and HA fragments have different shapes, the column was calibrated using human umbilical vein HA (Mr~2×10$^6$ D) and the HA fragments, F1, F2 and F3. Alternatively, to test the effect of HA and HA fragments isolated from urine on endothelial cell proliferation, the specimens were precipitated with trichloroacetic acid (5% v/v) at 4° C. for 4 h. The precipitation step was included in order to denature and remove any protein growth factors (e.g., basic-FGF) present in the urine. The trichloroacetic acid treated urine specimens were centrifuged; the supernatants were dialyzed against water, lyophilized, resuspended in PBS and then chromatographed on the Sepharose 6 CL-B column.

Mitogenic assay

Growing primary cultures of human lung microvessel endothelial cells (HMVEC-L), in their second or third passage, were obtained from Clonetics Corp. (San Diego, Calif.) and grown on 48-well culture plates in "Endothelial Cell Growth Medium" (Clonetics Corp., San Diego, Calif.). At 80% confluence, the cultures were pre-incubated in a serum-free and additive (bovine pituitary extract, EGF and hydrocortisone)-free basal medium (EBM) for 12 h at 37° C. Following pre-incubation, the cells were incubated for 18 h in fresh EBM containing HA or HA fragments of known lengths or peak HA fractions (I-V) isolated from patient urine. Following incubation, [$^3$H]-thymidine (1 $\mu$Ci/ml) was added to these cultures and the assay was terminated after a 2 h incubation as described previously (Lokeshwar et al., Protamine induces EGF-stimulated mitogenesis by increasing cell surface EGF receptor number: Implications for the existence of cryptic EGF receptor. J. Biol. Chem., 264: 19318–19326, 1989). The results presented are mean±s.d. from triplicate determinations.

Statistical analysis

The data presented as either mean HA concentration for individual patients or mean±SEM for each group of patients. The differences in the mean HA concentrations between various groups were assessed by the Dunn's multiple comparison test since the mean HA concentrations between groups showed a non-parametric distribution.

Determination of HA Concentration in Urine Specimens

An ELISA-like assay, involving the use of a biotinylated HA binding protein was used to determine the HA concentration in urine specimens. Because urinary HA levels (ng) were found to be influenced by the hydration status and urine output, these levels were normalized to urinary protein content (mg). The urinary HA levels were normalized to total protein rather than to creatinine because the normalization to protein was found to be less influenced by hematuria, a condition commonly found in bladder cancer patients (Soloway, The management of superficial bladder cancer. Cancer, 45: 1856–1865, 1980). The inventors compared the urinary HA levels between normal individuals (n=25) and those with bladder cancer (e.g., G1, G2 and G3 (including CIS), n=74). As controls, the enzyme levels of patients with GU conditions other than bladder cancer (e.g., BPH, prostate cancer, kidney stones, bacterial infections, cystitis, prostatitis, renal trauma and epididymitis (n=45)), were also measured in this study. As shown in FIG. 5A, the distribution of urinary HA levels among normal individuals and patients with other GU conditions is very similar and the HA levels of most of the individuals included in these two groups are <500 ng/mg. However, the urinary HA levels are uniformly elevated in bladder cancer patients, regardless of the tumor grade (e.g., G1, G2 and G3), and for most patients, these levels are >500 ng/mg (FIG. 5A).

The comparison of the mean urinary HA levels among various groups is shown in FIG. 5B. The mean urinary HA levels among normal individuals (223.5±31 ng/mg) and those with other GU conditions (347.5±34 ng/mg) do not vary significantly. The statistical analysis of these data by the Dunn's multiple comparisons test shows that the differences observed in the mean urinary HA levels among normal individuals and patients with other GU conditions are not statistically significant (P>0.05, Table 3). However, the urinary HA levels are significantly elevated (4–9 fold) among patients with G1 (1275±208.5 ng/mg), G2 (1459±341.5 ng/mg) or G3 (2142±335 ng/mg) bladder tumors. The Dunn's multiple comparisons test shows that the differences in the mean urinary HA levels of bladder cancer patients and those of normal individuals or other GU patients are statistically significant (P<0.001, Table 3). Nevertheless, the differences observed in the mean urinary HA concentrations of patients with different grades (e.g., G1, G2 and G3) of bladder tumors are not statistically significant (P>0.05, Table 3). These results show that an increase in urinary HA levels is indicative of a bladder tumor; however, it is not a predictor of tumor grade.

Table 3

Dunn's multiple comparisons test for comparing the mean urinary HA levels among normal individuals, patients with other GU conditions or bladder cancer. The data presented in FIG. 5 were analyzed using the Dunn's multiple comparisons test.

TABLE 3

| Comparison | Mean Difference | P value |
| --- | --- | --- |
| Normal vs. GU | −124 | P > 0.05 |
| Normal vs. G1 | −1051.5 | P < 0.001 |
| Normal vs. G2 | −1235.5 | P < 0.001 |
| Normal vs. G3 | −1918.5 | P < 0.001 |
| GU vs. G1 | −927.5 | P < 0.001 |
| GU vs. G2 | −111.5 | P < 0.001 |
| GU vs. G3 | −1794.5 | P < 0.001 |
| G1 vs. G2 | −184 | P > 0.05 |
| G1 vs. G3 | −867 | P < 0.001 |
| G2 vs. G3 | −683 | P > 0.05 |

The data on urinary HA levels were further analyzed to determine the specificity and sensitivity of the ELISA-like assay for detecting bladder cancer. As shown in Table 4, the overall specificity of this assay using 500 ng/mg as a minimum cut-off limit, was 92.8%. At the same cut-off limit, the sensitivity of this assay to detect bladder cancer was 91.9%. The analysis shows that the false positive and the false negative outcomes from this assay were 7.2% and 8.1% respectively.

Table 4

Determination of the sensitivity and specificity for the ELISA-like assay to detect bladder cancer. The data on individual urinary HA levels shown in FIG. 5A, were analyzed for sensitivity and specificity calculations using 500 ng/mg HA concentration as a minimum cut-off limit. The sample included 74 bladder cancer patients and individuals with no disease (n=25) or other GU conditions (e.g., cystitis, BPH, prostate cancer, bacterial infections, kidney stones, etc. n=45). Sensitivity=true positive results/total number of bladder cancer patients. Specificity=true negative results/total number of patients without bladder cancer. False-positive rate=false-positive results/total number of individuals without bladder cancer. False negative rate=false-negative results/total number of individuals with the disease.

a: The specificity for each group of individuals such as normals and patients with other GU conditions are 96% and 91.1% respectively.

b: The sensitivity of the ELISA-like assay for detecting the low-grade (G1) and low-stage (Ta) tumors was 88.7%. The sensitivity of the assay to detect high-grade ($\geq$G2) and high-stage ($\geq$T1) tumors was 92.7%.

TABLE 4

| Outcome | Urinary HA level |
| --- | --- |
| Sensitivity | [a]91.9% (68/74) |
| Specificity | [b]92.8% (65/70) |
| False-positive rate | 7.2% (5/70) |
| False-negative rate | 8.1% (6/74) |

Comparison of HA Concentrations in Bladder Tissues

To determine whether the increase in urinary HA levels is due to secretion of tumor-associated HA into the urine, the inventors examined HA levels in the tissue extracts prepared from normal bladder, low-grade TCCs (G1 tumor) and high-grade TCCs (G2+G3 tumors) using the ELISA-like assay. As shown in FIG. 6A, the HA levels are elevated in bladder tumor tissues, regardless of the tumor grade, as compared to those in normal bladder tissues. The mean HA levels present in the low-grade TCC tissues (29±10.5 μg/mg) and high-grade TCC tissues (46.5±16.5 μg/mg) are 3- and 5-fold higher than those present in the normal bladder tissues (9±2 μg/mg) respectively. As shown in Table 5, the differences in tissue HA levels among normal bladder specimens and bladder tumors (low-grade or high-grade TCC) are statistically significant (P<0.001). However, the differences in the HA levels present in the low-grade and high-grade TCCs tissues are not statistically significant (P>0.05, Table 5). These results show that there is a direct correlation between elevated urinary HA levels and increased tumor-associated HA.

Table 5

Dunn's multiple comparisons test for comparing mean HA levels among normal and bladder tumor tissues. The data presented in FIG. 6 was analyzed by the Dunn's multiple comparisons test. The low-grade and high-grade TCCs indicate the groups of individuals with either G1 or G2+G3 tumors respectively.

TABLE 5

| Comparison | Mean Difference | P value |
|---|---|---|
| Normal vs. low-grade TCCs | −20 | $P < 0.001$ |
| Normal vs. high-grade TCCs | −37.5 | $P < 0.001$ |
| Low-grade vs. High-grade TCCs | −17.5 | $P > 0.05$ |

Determination of Urinary HA Profile

It has been shown that small fragments of HA (3–25 disaccharide units) generated by the hyaluronidase digestion of HA, are angiogenic in vivo (West et al., Angiogenesis induced by degradation products of hyaluronic acid. Science, 228: 1324–1326, 1985). To determine whether such HA fragments are present in urine, the inventors examined the profiles of HA species that are present in the urine of normal individuals and patients with low-grade or high-grade TCC, using gel-filtration chromatography. The sizes of urinary HA species were determined by calibrating the column with high molecular mass HA (Mr~$2\times10^6$ dalton) and HA fragments of known lengths (F1 (10–15 disaccharide units), F2 (2–3 disaccharide units), and F3 (~2 disaccharide units). The F1 fragment has been shown to modulate various functions of bovine aortic endothelial cells (Banarjee and Toole, Hyaluronan binding protein in endothelial cell morphogenesis. J. Cell Biol., 119: 643–652, 1992). As shown in FIG. 7, the urine of normal individuals contains a small amount of HA and its size was intermediate between the high molecular mass HA and the F1 fragment. The urine of low-grade TCC patients contains a small amount of high molecular mass HA and a broad second peak of intermediate size HA (FIG. 7). The second peak appears to contain some amount of F1 fragment (FIG. 7). The HA profile of the high-grade TCC patients urine shows a complicated pattern. The profile consists of two large peaks, corresponding to the high-molecular mass HA and the F1 fragment. These two peaks are separated by a peak of the intermediate size HA (FIG. 7). In addition, the high-grade TCC patients urine contains two small HA peaks that correspond approximately to the F2 and F3 HA fragments (FIG. 7). These results show that although HA concentration was increased in all bladder cancer patients, HA profile was different among the low-grade and high-grade TCC patients.

Figure 8:
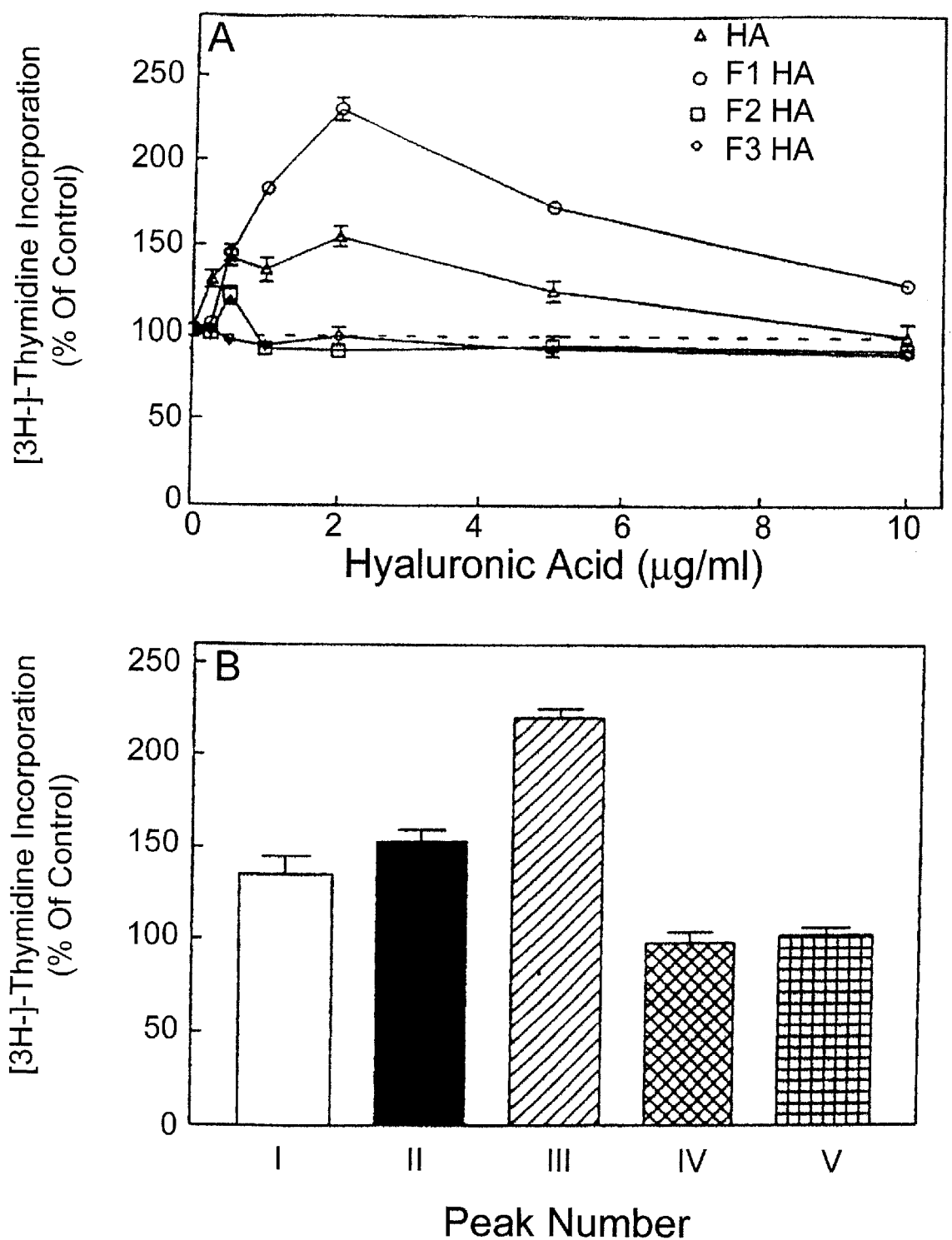

Effect of HA and HA Fragments on the Proliferation of Human Microvessel Endothelial Cells Using a [$^3$H]-thymidine incorporation assay, the inventors examined the effect of high-molecular mass HA and HA fragments (F1, F2 and F3), either generated in vitro or those isolated from the urine of high-grade TCC patients, on the proliferation of the primary cultures of human lung microvessel endothelial cells (HMVEC-L). As shown in FIG. 8A, the high-molecular mass HA and the F1 fragment induce a mitogenic response in HMVEC-L cells in a dose dependent manner and cause a maximum increase of 1.5-fold and 2.3-fold, at 2 μg/ml concentration, respectively. The F2 and F3 fragments are not mitogenic to these cells (FIG. 8A). Among the HA species that are isolated from the high-grade TCC patients urine, peak I (high-molecular mass HA) and peak II (intermediate size HA) induce a modest mitogenic response (1.2–1.3 fold) in HMVEC-L cells. However, the HA species present in peak III, which corresponds to the F1 fragment, induce a ~2.4-fold mitogenic response in HMVEC-L cells (FIG. 8). The very small HA fragments (peaks IV and V) that correspond to the F2 and F3 fragments, are not mitogenic. These results suggest that HA fragments that stimulate endothelial cell functions (e.g., proliferation) are present in the urine of high-grade TCC patients.

Figure 5:
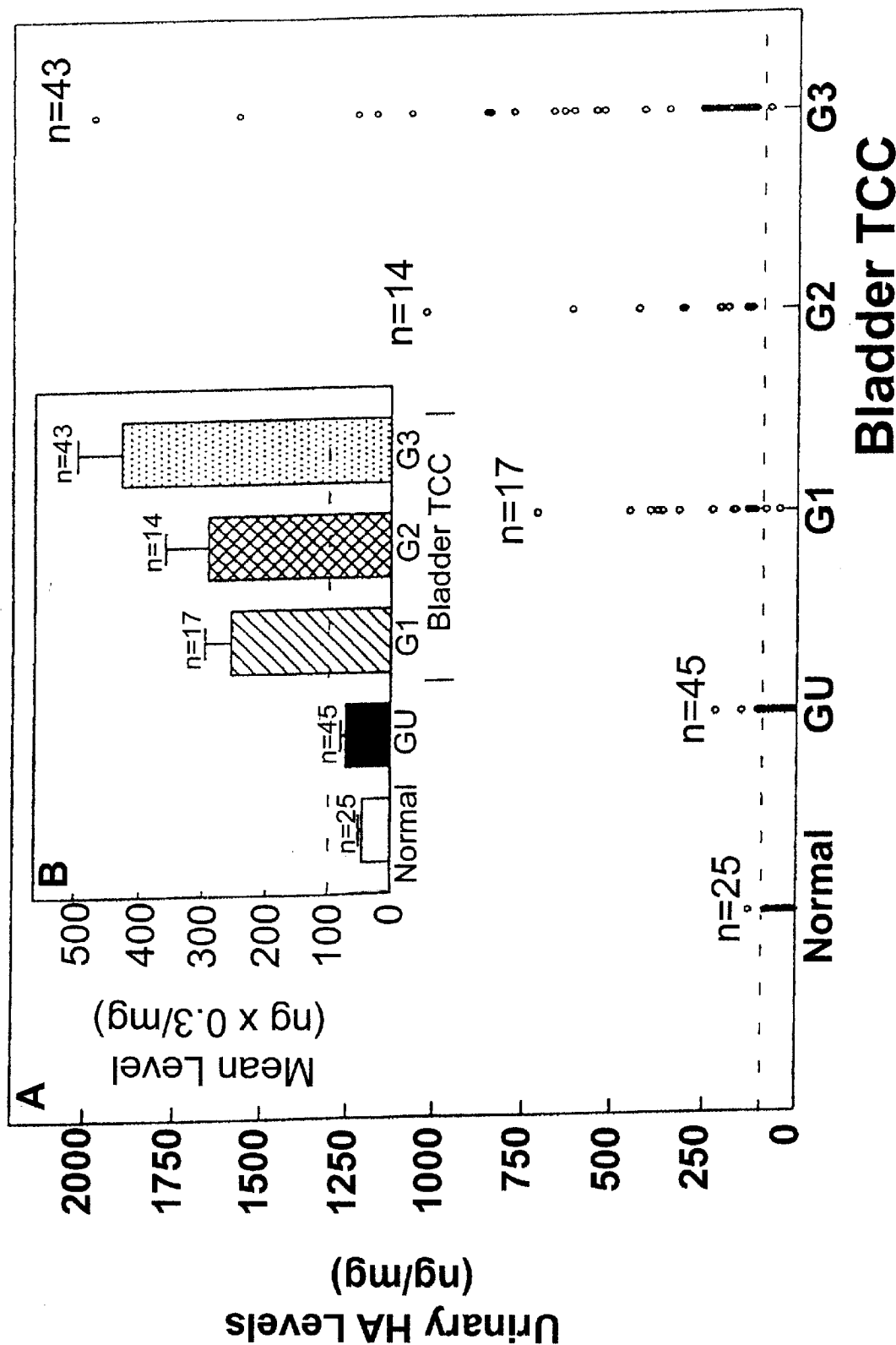
FIGS. 5A and B: Measurement of urinary HA levels by an ELISA-like assay. The urinary HA levels among different groups of individuals were measured as described in EXAMPLE 2 below.
Figure 6:
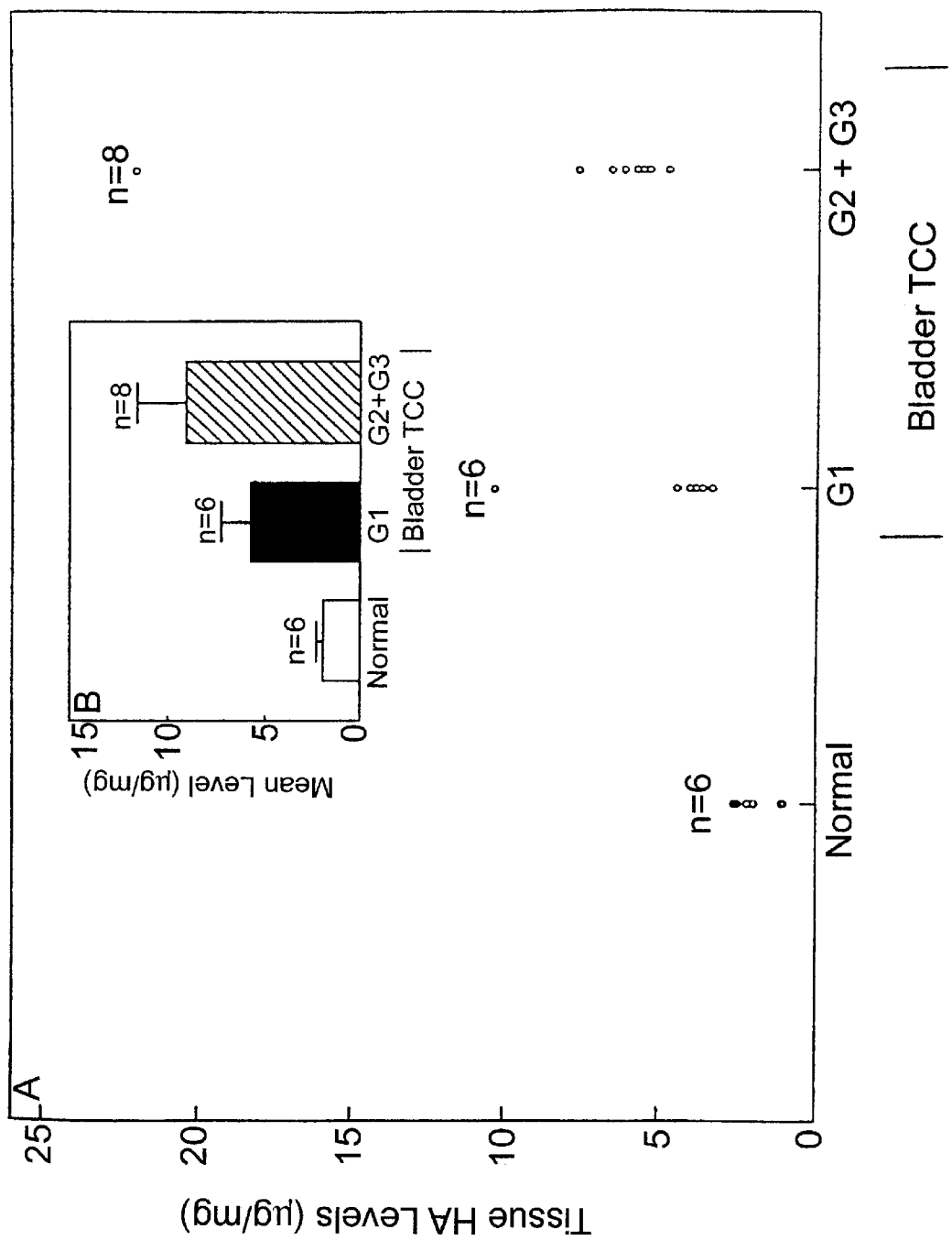

To summarize, urinary HA levels are significantly elevated (4–9 fold; FIG. 5) in all bladder cancer patients and show that urinary HA levels are useful as a marker for bladder cancer. The increase in the urinary HA levels of bladder cancer patients may be due to the direct secretion of tumor-associated HA in urine (FIG. 6).

The differences in the urinary profiles of normal, low-grade TCC and high-grade TCC patients indicate that size determination of urinary HA may be another indicator of the prognosis for bladder cancer. It should also be noted that the profile of HA species in bladder cancer is different from those found in the urine or sera of children with renal cancer (Lin et al., Urinary hyaluronic acid is a Wilms' tumor marker. J. Ped. Surg., 30: 304–308, 1995; Kumar et al., Sera of children with renal tumors contain low molecular mass hyaluronic acid. Int. J. Cancer, 44: 445–448, 1989). Therefore, the size of HA species and the pattern of their distribution may be different in tumors of different orgins as well as grade.

Example 3

Updated Studies and Data of Example 1

Hyaluronidase Determination

Urine Specimens

Voided (clean-catch) urine specimens were collected from 139 individuals under a protocol approved by the Institutional Review Board of University of Miami. The individuals were categorized into three groups. Group 1: normal (healthy) age-matched (30–70 yrs) individuals (n=20). Group 2: patients with other genito-urinary (GU) conditions (n=48) such as advanced prostate cancer (n=10), benign prostate hyperplasia (BPH; n=8), kidney stones (n=5), cystitis (n=12), urinary tract infections (n=8), prostatitis (n=2), epididymitis (n=1), and renal trauma (n=2). Group 3: patients with G1 (n=22, stage Ta), G2 (n=9, stages Ta–T2) or G3 (n=40) bladder tumors. The G3 subcategory included, 34 individuals with G3 tumors (stages T1–T4) and six individuals with carcinoma in situ (CIS). CIS is a subclass of high-grade tumors that are flat and superficial (confined to the urothelium). All specimens were collected and stored at −20° C. until assayed.

Tissue Specimens

Normal bladder tissues from adults (21–50 years) were obtained from organ donors. Tissue procurement was performed according to relevant state and federal regulations. Bladder tumor tissues were obtained from patients (41–72 years) undergoing cystectomy or transurethral resection of the tumor. Tissue hyaluronidase levels were analyzed in three groups of patients. Group 1: normal bladder (n=6). Group 2: low-grade TCCs (G1, n=6). Group 3: high-grade TCCs (G2, n=2; G3, n=6). To evaluate the grade, each tumor specimen was split and the mirror image segment was fixed in formalin, embedded in paraffin and analyzed histologically.

Tissue Extracts

Tissue specimens (≈0.5–1 g) were homogenized in a buffer containing 5 mM HEPES pH 7.2 and 1 mM benzamidine-HCl. The homogenates were clarified by centrifugation at 40,000×g for 30 min and the clear extracts were assayed.

Substrate (HA)-gel Assay

Urine samples (≈20 μg protein) were electrophoresed under either non-denaturing conditions on a 7.5% polyacrylamide gel or under denaturing conditions on a 12% SDS-polyacrylamide gel, containing 0.17 mg/ml human umbilical cord HA (Sigma Chemical Co., St. Louis, Mo.). Following electrophoresis, the gel was incubated in a hyaluronidase assay buffer (0.1 M sodium formate, 0.15 M NaCl, pH 4.3), for enzymatic digestion, at 37° C. for 16–18 h. The proteins electrophoresed on a denaturing gel were renatured by incubating the gel in a 3% Triton X-100 solution prior to incubation in the hyaluronidase assay buffer. Following incubation, the gels were stained sequentially with 0.5% Alcian blue and 0.15% Coomassie blue solutions, and destained with 10% methanol/10% acetic acid solution. The presence of hyaluronidase was inferred from the unstained (clear) area(s) in the gel, as described previously (Lokeshwar, V. B., Lokeshwar, B. L., Pham, H. T., and Block, N. L. Association of hyaluronidase, a matrix-degrading enzyme with prostate cancer progression. Cancer Res., 56: 651–657, 1996; Gütenhoner et al., Substrate gel assay for hyaluronidase activity. Matrix, 12: 388–396, 1992).

SDS-Polyacrylamide Gel Electrophoresis (SDS-PAGE) and Silver Staining

Urine specimens (~20 μg protein) were analyzed by 12% SDS-PAGE and then silver stained to reveal the total urinary protein profile.

ELISA-like Assay for Hyaluronidase Activity 96-well microtiter plates coated with 200 μg/ml HA, were incubated with serial dilutions of urine specimens, tissue extracts or Streptomyces hyaluronidase (CalBiochem, San Diego, Calif.) in hyaluronidase assay buffer containing 0.2 mg/ml BSA at 37° C. for 16–18 h. Following incubation, the degraded HA was washed off and HA remaining in the wells was quantitated using a biotinylated cartilage HA-binding protein (Tengblad, Affinity chromatography on immobilized hyaluronate and its application to the isolation of hyaluronate binding proteins from cartilage. Biochim. Biophys. Acta, 578: 281–289, 1979), an avidin-biotin detection system and ABTS substrate kit (Vector Laboratories, Burlingame, Calif.) as described previously (Lokeshwar et al., Association of hyaluronidase, a matrix-degrading enzyme with prostate cancer progression. Cancer Res., 56: 651–657, 1996; Stern and Stern, An ELISA-like assay for hyaluronidase and hyaluronidase inhibitor. Matrix, 12: 397–403, 1992). The absorbance was read at 405 nm in a microtiter plate reader. In each assay, the maximum absorbance $(A_{max})_{405\ nm}$ was obtained by incubating the HA-coated wells with buffer alone in the absence of any hyaluronidase. $(A_{min})_{405\ nm}$ was obtained by incubation of hyaluronidase in uncoated wells. A standard graph was prepared by plotting absorbance (405 nm) versus Streptomyces hyaluronidase activity (mU/ml). Using this graph, the hyaluronidase concentration in each dilution of either urine or tissue extract was calculated. The mean hyaluronidase activity in each sample was calculated by measuring the activity in seven separate dilutions. All activity determinations (mU/ml) were normalized to protein concentration (mg/ml). To determine the pH activity profile of bladder tumor-derived hyaluronidase, the HA-coated wells were incubated with aliquots of urine or tissue extracts in formate-NaCl buffer at various pH (2.0–7.0). The results are expressed as $(A_{max}-A_{sample})_{405\ nm} \times 100$. The maximum difference is designated as 100%, and the data are expressed as a percentage of maximum.

Statistical Analysis

The data are presented as either mean hyaluronidase activity for individual patients or mean±SEM for each group of patients. The differences between groups were assessed by the Tukey-Kramer multiple comparisons test since the mean hyaluronidase levels showed a parametric distribution.

Detection of Urinary Hyaluronidase Activity (a) Substrate Gel Assay

Hyaluronidase activity in urine samples was detected using a sensitive substrate (HA)-gel technique (Lokeshwar et al., Association of hyaluronidase, a matrix-degrading enzyme with prostate cancer progression. Cancer Res., 56: 651–657, 1996; Gütenhoner et al., Substrate gel assay for hyaluronidase activity. Matrix, 12: 388–396, 1992). As shown in FIG. 9, little or no HA digestion was observed in lanes containing urine specimens of normal individuals (lanes 1 and 2) and patients with low-grade TCC (lanes 3 and 4). However, a broad band of HA digestion is observed in specimens from high-grade TCC patients (lanes 5 and 6), suggesting that these samples contain significant amounts of hyaluronidase activity.

(b) Quantitative Determination of Urinary Hyaluronidase Activity by an ELISA-like Assay Accurate quantitation of the hyaluronidase levels in urine samples (n=139) was accomplished by an ELISA-like assay (Lokeshwar et al., Association of hyaluronidase, a matrix-degrading enzyme with prostate cancer progression. Cancer Res., 56:651–657, 1996. The variation in hydration status and urine output of individuals was corrected by normalizing the hyaluronidase levels (mU) to urinary protein concentration (mg). The hyaluronidase levels were normalized to urinary protein concentrations rather than creatinine since the normalization to protein was found to be less influenced by hematuria, a condition commonly found in bladder cancer patients (Soloway, The management of superficial bladder cancer. Cancer, 45: 1856–1865, 1980). The inventors compared the urinary hyaluronidase levels between normal individuals (n=20) and those with bladder cancer (e.g., G1, G2 and G3 tumors and CIS, n=71). As controls, the enzyme levels of patients with GU conditions other than TCC (e.g., BPH, prostate cancer, kidney stones, bacterial infections and cystitis, renal trauma, prostatitis, and epididymitis, n=48) were also included in the study. As shown in FIG. 10A, the distribution of urinary hyaluronidase levels among normal individuals and patients with either low-grade (G1) bladder tumors or other GU conditions is very similar. Furthermore, the enzyme levels of most of the individuals included in these three groups are <10 mU/mg. However, the hyaluronidase levels are elevated among all patients with intermediate (G2) to high-grade (G3) bladder tumors and are >10 mU/mg (FIG. 10A).

The comparison of the mean urinary hyaluronidase levels among various groups is shown in FIG. 10B. The mean urinary hyaluronidase levels among normal individuals (4.2±1.2 mU/mg), those with other GU conditions (7.4±1.4 mU/mg), or G1 tumors (6.5±1.7 mU/mg) do not vary significantly. However, the levels are significantly elevated among patients with G2 tumors (32±6.1 mU/mg) or G3 tumors (34.3±3.1 mU/mg). The mean urinary hyaluronidase levels of all patients with G2 or G3 tumors combined (33.4±4.5 mU/mg) are 5–9 fold higher than those in normal individuals and patients with other GU conditions or G1 bladder tumors. It is important to note that the urinary hyaluronidase levels are elevated 6–11 fold (46±5.9 mU/mg) in all patients with CIS (a subclass of high-grade bladder TCCs that are superficial and flat). These results show that all high-grade bladder cancer patients examined here have elevated urinary hyaluronidase levels prior to the occurrence of invasive disease.

The statistical significance of the observed differences in the mean hyaluronidase levels among various categories of patients was assessed using the Tukey-Kramer multiple comparisons test. As shown in Table 6, the differences between the mean hyaluronidase levels of normal individuals and patients with G1 bladder tumors or other GU conditions are not statistically significant (P>0.05; Table 6). But those differences between normal individuals/other GU patients and patients with either G2 or G3 tumors are statistically significant (P<0.001, Table 6). The differences in the mean hyaluronidase levels among patients with G1 tumors and G2 or G3 tumors are also statistically significant (P<0.001, Table 6). The differences nevertheless, in the mean enzyme levels among patients with either G2 or G3 tumors are not statistically significant (P>0.05). Therefore, these results show that the urinary hyaluronidase levels are elevated in all intermediate to high-grade cancer patients.

Table 6

Tukey-Kramer multiple comparisons test for comparing mean urinary hyaluronidase levels in normal individuals and bladder cancer patients. The data presented in FIG. 10 were analyzed statistically using the Tukey-Kramer multiple comparisons test. If the q value is greater than 3.916, then the P value is less than 0.05.

TABLE 6

| Comparison | Mean Difference | q | P value |
| --- | --- | --- | --- |
| Normal vs GU | −3.142 | 1.156 | P > 0.05 |
| Normal vs G1 | −2.175 | 0.709 | P > 0.05 |
| Normal vs G2 | −27.725 | 7.126 | P < 0.001 |
| Normal vs G3 | −30.033 | 10.834 | P < 0.001 |
| GU vs G1 | 0.967 | 0.398 | P > 0.05 |
| GU vs G2 | −24.583 | 7.210 | P < 0.001 |
| GU vs G3 | −26.891 | 13.163 | P < 0.001 |
| G1 vs G2 | −25.550 | 6.915 | P < 0.001 |
| G1 vs G3 | −27.858 | 11.189 | P < 0.001 |
| G2 vs G3 | −2.308 | 0.668 | P > 0.05 |

The data on urinary hyaluronidase levels were further analyzed to determine the specificity and sensitivity of the ELISA-like assay for detecting high-grade TCCs. As shown in Table 7, the overall specificity of this ELISA-like assay, using 10 mU/mg as a minimum cut-off limit, was 88.8%. At the same cut-off limit the sensitivity of this assay to detect high-grade TCCs was 100% (i.e., not a single high-grade tumor was missed). The analysis shows that false positive and false negative outcomes from this assay were 11.2% and 0% respectively.

Table 7

Determination of sensitivity and specificity for the ELISA-like assay to detect high-grade bladder cancer. The data on urinary hyaluronidase levels shown in FIG. 10 were analyzed for sensitivity and specificity calculations using 10 mU/mg as a minimum cut-off limit for an enzyme level. The sample included 49 high-grade TCC (G2 and G3 tumor) patients, and 90 individuals with no disease (n=20) or other GU conditions (e.g., cystitis, bacterial infections, BPH, kidney stones, prostate cancer, etc. n=48) or low-grade TCCs (G1 tumor, n=22). Sensitivity=true positive results/total number high-grade TCC patients. Specificity=true negative results/total number of patients without high-grade TCC. False negative rate=false-negative results/total number of patients with high-grade TCCs. False-positive rate= false-positive results/total number of individuals without high-grade TCCs.

a: The specificity for each group of individuals such as normals, patients with other GU conditions, and low-grade TCCs patients are 93.7%, 84.5% and 90.9% respectively.

TABLE 7

| Outcome | Urinary hyaluronidase level |
| --- | --- |
| Sensitivity | 100% (49/49) |
| Specificity | [a]88.8% (80/90) |
| False-positive | 11.6% (10/90) |
| False-negative | 0% (0/49) |

Examination of Hyaluronidase Activity in Bladder Tissue Extracts

Since these studies showed that urinary hyaluronidase levels are elevated in high-grade bladder tumor patients, the inventors hypothesized that this increase is a result of the secretion of a tumor-derived hyaluronidase(s) in the urine. Thus, they tested for the presence of hyaluronidase activity in tissue extracts prepared from normal bladder, low-grade TCCs (G1 tumors), and high-grade TCCs (G2 and G3 tumors) using the ELISA-like assay. As shown in FIG. 11A, the hyaluronidase levels in normal bladder and in G1 tumor tissues are very similar. However, the G2 and G3 tumor tissue extracts show significantly elevated hyaluronidase levels (FIG. 11A). The mean hyaluronidase levels present in the G2 and G3 tumor tissues (13.2±1.2 mU/mg) are indeed 6–7 fold higher than those present in normal bladder (1.9±0.35 mU/mg) and G1 tumor (2.7±0.61 mU/mg) tissues (FIG. 11B). The statistical analysis of these data by the Tukey-Kramer multiple comparisons test shows that the observed differences in the mean hyaluronidase activity between the normal and G2 and G3 tumor tissues (P<0.001), but not those between normal bladder and G1 tumor tissues (P>0.05), are statistically significant (Table 8). Furthermore, differences in the mean enzyme levels between G1 tumors and G2 or G3 tumors are statistically significant (P<0.001, Table 8). Thus the elevation in both urine and tissue hyaluronidase levels is associated with intermediate to high-grade TCCs of the bladder.

Table 8

Tukey Kramer multiple comparisons test for comparing mean tissue hyaluronidase levels in normal individuals and bladder cancer patients. The data presented in FIG. 11 were analyzed statistically using the Tukey Kramer multiple comparisons test. If the q value is greater than 2.655, then the P value is less than 0.05.

TABLE 8

| Comparison | Mean Difference | q | P value |
| --- | --- | --- | --- |
| Normal vs Low-grade TCCs | −0.0800 | 0.7946 | P > 0.05 |
| Normal vs High-grade TCCs | −11.371 | 12.074 | P < 0.001 |
| Low-grade TCCs vs High-grade TCCs | −10.571 | 11.225 | P < 0.001 |

Characterization of the Bladder Tumor-associated Hyaluronidase Activity

The pH activity profile of the bladder tumor-associated hyaluronidase activity was determined using the ELISA-like assay. As shown in FIG. 12, the hyaluronidase activity present in the urine and tumor (G3) tissue of a high-grade TCC patient has a distinct pH optimum, 4.3, for HA degradation. The pH optimum for bladder tumor-associated hyaluronidase activity is different from those reported for hyaluronidases from other sources such as serum, liver, kidney, testis and prostate (Gold, Purification and properties of hyaluronidase from human liver. Biochem. J., 205: 69–74, 1982; Stern et al., Hyaluronidase levels in urine from Wilms' tumor patients. J. Natl. Canc. Inst., 83: 1569–1574, 1991; Lokeshwar et al., Association of hyaluronidase, a matrix-degrading enzyme with prostate cancer progression. Cancer Res., 56: 651–657, 1996; Afify et al., Purification and characterization of human serum hyaluronidase. Arch. Biochem. Biophys., 305: 434–441, 1993; Salegui et al., A comparison of serum and testicular hyaluronidase. Arch. Biochem. Biophys., 121: 548–554, 1967).

Figure 13:
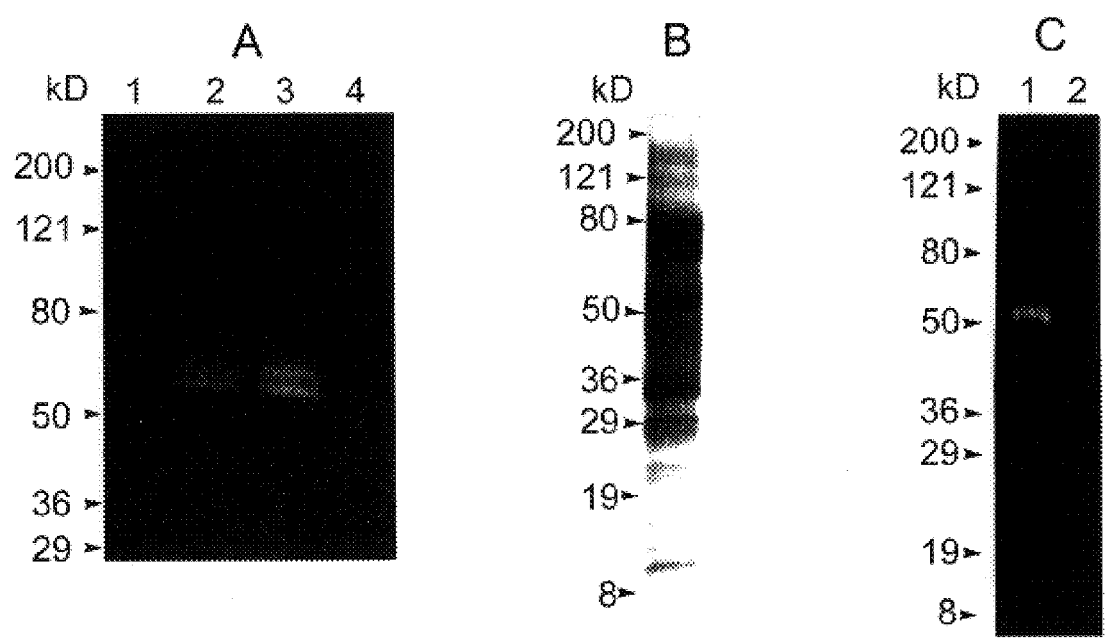

Next a substrate (HA) SDS-PAGE technique was used to determine the relative molecular mass of bladder tumor-derived hyaluronidase (Lokeshwar et al., Association of hyaluronidase, a matrix-degrading enzyme with prostate cancer progression. Cancer Res., 56: 651–657, 1996; G ütenhoner et al., Substrate gel assay for hyaluronidase activity. Matrix, 12: 388–396, 1992). Urine specimens (40 µg protein) from both a normal individual and bladder cancer patients were analyzed by substrate (HA) SDS-PAGE. As shown in FIG. 13A, two hyaluronidase proteins of relative Mr 65 kD (p65) and 55 kD (p55) are present in the urine of patients with G2 (lane 2), G3 (lane 3) tumors. However, no hyaluronidase bands are detected in the urine of a patient with G1 tumor (lane 1) or a normal individual (lane 4) at the same total urine protein concentration. To determine whether the p65 and p55 are the major protein species in the urine of high-grade bladder cancer patients, a urine specimen from a G3 bladder cancer patient was analyzed by SDS-PAGE and silver staining to reveal the total protein profile. As shown in FIG. 13B, the high-grade bladder cancer patient urine contains several proteins. However, p65 and p55 are not the major proteins in the urine and can not be identified among other proteins. This is not surprising since both the ELISA-like assay and the substrate gel assay detect the activity rather than protein and both assays are highly sensitive. In addition, no differences were observed in the urinary protein profiles of high-grade bladder cancer patient and normal individuals (data not shown). To determine whether p55 and p65 are expressed in G3 tumors and normal bladder, tissue extracts (~40 µg protein) prepared from these sources were analyzed by substrate (HA) SDS-PAGE. As shown in FIG. 13, both p65 and p55 are present in G3 tumor tissue extract (left lane), but as expected, not in the normal bladder tissue (right lane). It is interesting to note that only a single hyaluronidase protein is expressed in other tissues (Stern et al., Hyaluronidase levels in urine from Wilms' tumor patients; J. Natl. Canc. Inst., 83: 1569–1574, 1991; Lokeshwar et al., Association of hyaluronidase, a matrix-degrading enzyme with prostate cancer progression. Cancer Res., 56: 651–657, 1996; Afify et al., Purification and characterization of human serum hyaluronidase. Arch. Biochem. Biophys., 305: 434–441, 1993; Salegui et al., A comparison of serum and testicular hyaluronidase. Arch. Biochem. Biophys., 121: 548–554, 1967).

These data show that urinary hyaluronidase levels are significantly elevated (for instance, about 5–9 fold) in patients with high-grade (G2 and G3 tumors) bladder TCC and indicate that hyaluronidase can be a useful urine marker for detecting high-grade bladder tumors.

The increase in both the urinary and tissue hyaluronidase levels suggests that a tumor-derived hyaluronidase(s) may be secreted into the urine. Preliminary data show that the hyaluronidase(s) is secreted by bladder tumor epithelial cells (unpublished results). (Also see, Lokeshwar et al., Association of hyaluronidase, a matrix-degrading enzyme with prostate cancer progression. Cancer Res., 56: 651–657, 1996). The identification of two hyaluronidase proteins (p65 and p55) having a different pH optimum from other hyaluronidases suggests that the bladder tumor-derived hyaluronidases may be new members of this growing family.

Example 4

Updated Studies and Data of Example 1
Further Hyaluronic Acid and Hyaluronidase Determinations In two separate studies (Study A and Study B), the inventors examined the urinary HA and HAase levels of 356 individuals using substantially the same procedures as described in EXAMPLES 1, 2 and 3.

Study A

In Study A involving 191 individuals, urinary HA levels expressed as ng/mg protein (HA test), were found to be elevated 4–7 fold in all bladder cancer patients (1488.5±221, n=121) regardless of tumor grade, as compared to those in normals (223.5±15.5, n=25) and other genito-urinary (GU) patients (371±39, n=45) ($P<0.001$). The GU patients included patients with benign prostatic hyperplasia (BPH), kidney stones, urinary tract infections, cystitis, prostate cancer, prostatitis, epididymitis, impotence. The sensitivity and specificity of the test to detect bladder cancer patients were calculated using 500 ng HA/mg protein as a minimum cut-off limit (Table 9). In the same study, the urinary HAase levels expressed as mU/mg protein (HAase test), were found to be elevated 4–7 fold in G2 and G3 bladder cancer patients (31.4±3.6) as compared to those in G1 bladder cancer patients (6.3±1.1), other GU patients (7.4±1.4) and normals (4.4±0.8) ($P<0.001$). The sensitivity and specificity of the HAase test were calculated using 10 mU/mg protein as a minimum cut-off limit (Table 9).

Table 9

Determination of the sensitivity, specificity, false-positive and false-negative rates and accuracy of the HA-HAase test in Study A. The data were obtained from Study A in which a total of 191 individuals were tested. The HA test detects all bladder cancer patients but the HAase test detects the high-grade (grades G2, G3 and carcinoma in situ (CIS)) bladder cancer patients.

TABLE 9

| Category | HA Test | HAase Test |
| --- | --- | --- |
| Sensitivity | 88.9% | 92.9% |
| Specificity | 88.6% | 88.7% |
| False-negative rate | 11.1% | 7.1% |
| False-positive rate | 11.4% | 11.3% |
| Accuracy | 88% | 90% |

Study B

To evaluate the sensitivity and specificity of the HA-HAase urine test, the inventors conducted a blinded study involving 165 individuals. The subjects included 51 bladder cancer patients, 10 normals and 114 patients with other GU conditions. The bladder cancer category of patients included 41 patients with the disease and 10 individuals with a history of bladder cancer but no disease at the time of testing. The data are presented in Table 10.

Table 10

Determination of the sensitivity, specificity, false-positive and false negative rates and accuracy of the HA-HAase test in Study B. This was a blinded study involving 165 individuals. It is noted that both tests when combined missed only two of the 41 bladder cancer patients, for an overall sensitivity of 95.1%.

TABLE 10

| Category | HA Test | HAase Test |
|---|---|---|
| Sensitivity | 92.5% | 90.4% |
| Specificity | 91.1% | 91.2% |
| False-negative rate | 7.5% | 9.6% |
| False-positive rate | 8.9% | 8.8% |
| Accuracy | 92% | 88% |

The results indicated that the combined sensitivity of the HA-HAase test was higher than either of the tests alone. This is because, in some cases, high-grade, high-stage bladder cancer patients gave a false negative result in the HA test but the HAase test was a true positive; presumably, because the high hyaluronidase activity degraded the hyaluronic acid present in the urine resulting in an apparent HA level less than the cut-off limit.

These studies show that HA-HAase urine test is a simple, non-invasive, highly sensitive and specific method for detecting bladder cancer and evaluating its grade.

Analysis of the Sensitivity of HA and HAase Tests by Tumor Grade and Stage (a) HA Test For sensitivity determination, 500 ng/mg protein for the HA level was set as a minimum cut-off limit. The bladder cancer patients include 121 and 36 TCC patients from Study A and Study B respectively.

Table 11

Sensitivity of HA test by tumor grade. The G1 category of bladder cancer (BCa) patients includes 6 patients with G1–2. The G3 category includes 25 CIS patients.

Table 12

Sensitivity of HA test by tumor stage. The grades of tumors at various pathological stages were as follows: G1Ta (n=41), G2Ta (n=15), G3Ta (n=5), G1T1 (n=1), G2/G3T1 (n=16), G2/G3 T2+ (n=55) and G3CIS (n=25).

TABLE 11

| Grade | # of BCa Patients | # of True Positives | Sensitivity |
|---|---|---|---|
| G1 | 41 | 37 | 90% |
| G2 | 24 | 23 | 96% |
| G3 | 92 | 81 | 88% |

TABLE 12

| Stage | # of Patients | # of True Positives | Sensitivity |
|---|---|---|---|
| Ta | 60 | 54 | 90% |
| T1 | 17 | 15 | 88% |
| T2+ | 55 | 50 | 92% |
| CIS | 25 | 24 | 96% |

As shown in Tables 11 and 12 the HA test detected G1, G2 and G3 bladder tumors with similar sensitivity, i.e., 90% (G1), 96% (G2) and 88% (G3). The sensitivity values for HA test to detect bladder tumors of various stages are also very similar. For example, the HA test detected tumors of stages Ta, T1, T2+ and CIS with sensitivity values of 90%, 88%, 92% and 96% respectively. These results demonstrate that the HA test detects bladder cancer patients regardless of the tumor grade or stage.

(b) HAase Test

For sensitivity determination, 10 mU/mg protein for the HAase level was set as a minimum cut-off limit. The bladder cancer patients include 121 and 36 TCC patients from Study A and Study B respectively.

Table 13

Sensitivity of the HAase test by tumor grade. Five G1 bladder cancer (BCa) patients had HAase levels >10 mU/mg. These patients were considered as false positives and were included in the specificity determination. In addition, 2 G1Ta patients had urinary HAase values the same as the cut-off limit (10 mU/mg protein). The G1 category of patients included 40 G1 Ta patients and one G1T1 patient.

Table 14

Sensitivity of the HAase test by tumor stage. The sensitivity values are calculated for high-grade tumors (G2+G3) except for CIS which is a sub-class of G3 tumors.

TABLE 13

| Grade | # of Patients | # of True Positives | Sensitivity |
|---|---|---|---|
| G1 | 41 | 5 | 12.1% |
| G2 | 24 | 21 | 88% |
| G3 | 92 | 84 | 91.3% |

TABLE 14

| Stage | # of Patients | # of True Positives | Sensitivity |
|---|---|---|---|
| Ta | 20 | 17 | 85% |
| T1 | 16 | 14 | 87.6% |
| T2+ | 55 | 50 | 91% |
| CIS | 25 | 22 | 88% |

As sown in Table 13, the HAase test detected G1, G2 and G3 bladder tumors with sensitivity values of 12.1%, 88% and 91.3%. This suggested that the HAase test preferentially detected intermediate- to high-grade bladder tumors ($\geq$G2). However, the results presented in Table 14 show that the HAase test detects high-grade bladder tumors of all stages with very similar sensitivity. For example, the HAase test detected high-grade bladder tumors of stages Ta, T1, T2+ and CIS with a sensitivity of 85%, 87.6%, 91% and 88% respectively. This also suggest that the HAase test is capable of detecting high-grade tumors prior to invasion (stages Ta or T1) with high sensitivity and can be used for the early detection of these class of bladder tumors.

These results show that the HA-HAase test can be used as a screening test to detect bladder cancer patients and to evaluate its grade. The HA test detects bladder cancer patients regardless of the tumor grade; the HAase test preferentially detects high-grade bladder cancer patients. The key to improve the survival of bladder cancer patients is to detect high-grade bladder cancer patients early prior to invasion. With the current mode of detection, the probability of detecting G3 tumors that are low-stage (Ta) is very low.

The HAase test, however, is equally sensitive in detecting both the high-grade low-stage and high-grade high-stage tumors. In addition, the HAase test also detects CIS, a subclass of G3 tumors which is pre-invasive but highly aggressive, with high sensitivity. Thus using HAase test as a screening test, it is possible to detect the high-grade bladder cancer patients early, prior to the occurrence of an invasive disease. Therefore, the combined use of the HA-HAase test will allow the screening of bladder cancer patients and early detection of high-grade tumors in a simple inexpensive and non-invasive manner. Such a screening may then improve the prognosis of bladder cancer patients in general and high-grade bladder cancer in particular.

It is important to note that although the majority of the bladder cancer patients included in this study had TCC of the bladder, the HA-HAase test also detected all of the adenocarcinoma (n=3) and squamous cell carcinoma (n=1) patients who were included in the blinded study (Study B). Thus, the HA-HAase test may also be useful in detecting other rare malignancies of the bladder.

Specificity Trial

To determine the specificity of the HA-HAase test the inventors tested both normal healthy volunteers and patients with other GU conditions. In study A, 70 individuals were included in the specificity trial. These 70 individuals included, 22 normals and 48 with GU conditions other than bladder cancer. The GU category included patients with prostate cancer (n=10); benign prostatic hyperplasia (BPH, n=8); kidney stones (n=5), cystitis (n=12), urinary tract infections (n=8), prostatitis (n=2), epididymitis (n=1) and renal trauma (n=2). As mentioned above, the specificities of the HA and HAase test were 88.6% and 88.7% respectively. For determining the specificity of the HAase test, patients with G1 disease (n=35) were included in the calculation.

In Study B, which was a blinded study, the specificity trial included 124 individuals (15 normals, 99 patients with GU conditions other than bladder cancer and 10 patients with a history of bladder cancer but no cystoscopic evidence of the disease at the time of testing). The GU category included patients with prostate cancer (n=37), post-radical prostatectomy (n=12), kidney/ureteral/urethral cancer (n=6), BPH (n=17), ureteral/kidney/bladder stone (n=5), testicular cancer (n=2), urinary tract infections (n=5), hematuria (n=2), cystitis (n=3), impotence (n=2), urinary retention (n=1), incontinence (n=1), renal colic (n=1), urethral stricture (n=1), seminal vesiculitis/prostatitis/epididymitis (n=3), bladder neck contraction (n=1), scrotal hematoma (n=1), vasectomy (n=1). As mentioned above, in Study B the specificities of the HA and the HAase tests were 91.1% and 91.2% respectively. For determining the specificity of the HAase test, patients with G1 disease (n=6) were included in the calculation.

In summary, the HA test detects bladder cancer regardless of the tumor grade. The HAase test however, preferentially detects high-grade bladder cancer. Thus by running both assays simultaneously, one can screen for bladder cancer and also get an idea about its grade. In addition in the blinded study (i.e., Study B), both the HA and HAase tests combined missed only 2 out of the 41 bladder cancer patients. Thus the overall sensitivity of the combined HA-HAase test (95%) was slightly better than the individual HA (92.5%) and HAase (92.5%) respectively.

Comparison of the HA-HAase Test with BARD BTA and NMP22™

According to published reports in peer reviewed scientific journals, both BTA and NMP22™ tests have been used to follow-up bladder cancer patients in order to detect bladder cancer recurrence. These tests have not been used as screening tests. As mentioned above, in an multi-center trial Sarosdy et al. have reported that the overall sensitivity of the BTA test to detect bladder cancer, regardless of the tumor grade, was ~40%.

In a study of 90 patients with a history of bladder cancer, the NMP22™ detected 23 out of 33 bladder cancer recurrences (overall sensitivity 70%). In addition, the NMP22™ detected all bladder cancer patients with invasive disease.

The comparison of HA-HAase test with BTA and NMP22™ is shown in Tables 15 and 16. As shown in Table 15 and 16, the HA-HAase test is better than either the BTA or NMP22™ test with respect to sensitivity, specificity, and prevalence related parameters in detecting bladder cancer.

Table 15

Comparison of BTA, NMP22™ and HA-HAase tests with respect to sensitivity and specificity. The BTA study "a" included 499 patients and study "b" included 60 patients. The NMP22™ study included 90 patients and the HA-HAase study included 356 patients.

Table 16

Comparison of BTA, NMP22™ and HA-HAase tests with respect to prevalence related parameters. The BTA study included 499 patients, the NMP22™ study included 90 patients, and the HA-HAase study included 356 patients. PPV: positive predictive value; NPV: negative predictive value.

TABLE 15

| Category | BTA | NMP22 ™ | HA-HAase |
|---|---|---|---|
| Sensitivity | [a]40% [b]65% | [c]70% | 92.3% |
| Specificity | [a]81–95% | [c]79% | 87.9% |

TABLE 16

| Category | BTA | NMP22 ™ | HA-HAase |
|---|---|---|---|
| Prevalence | [a]39% | [b]29.5% | 24.8% |
| PPV | 71% | 58% | 80% |
| NPV | 87% | 86% | 96.6% |

Sarosdy et al., Results of a multicenter trial using the BTA test to monitor for and diagnose recurrent bladder cancer, J. Urol., 154: 379–384, 1995.
D'Hallewin and Baert, Initial evaluation of the bladder tumor antigen test in superficial bladder cancer. J. Urol., 155:475–476, 1995.
Soloway et al., Use of a new tumor marker NMP22 in the detection of occult or rapidly recurring transitional cell carcinoma of the urinary tract following surgical treatment. J. Urol., 156: 363–367, 1996.
Sarosdy et al., Results of a multicenter trial using the BTA test to monitor for and diagnose recurrent bladder cancer, J. Urol., 154: 379–384, 1995.
Soloway et al., Use of a new tumor marker NMP22 in the detection of occult or rapidly recurring transitional cell carcinoma of the urinary tract following surgical treatment. J. Urol., 156: 363–367, 1996.

In a study in which the inventors followed ten patients with a history of bladder cancer for a period of one year to monitor for recurrence; the HA-HAase test detected all six recurrences (overall sensitivity 100%) in this study. In fact, the HA-HAase test detected four recurrences 3–6 mos. prior to the cystoscopic detection of the tumor. Thus in addition to being a screening test, the HA-HAase test can be used to monitor tumor recurrence.

Analysis of Bladder Cancer Other Than TCC

As is well known, TCCs comprise the majority (90–95%) of bladder tumors. The squamous and adenocarcinomas make up the remaining bladder tumors. The inventors analyzed three samples from adenocarcinoma and one from the squamous cell carcinoma patients. All of these tumors were detected by the HA-HAase test. This is indicative that the HA-HAase test of the inventions can detect all types of bladder tumors.

Example 5
Monitoring of Treatment Efficacy and Recurrence of Bladder Cancer by HA-HAase Urine Test In Study #1, the inventors compared pre- and post-treatment urinary HA and HAase levels of 25 bladder cancer patients. The results were compared to cystoscopy and cytology. For those patients who had undergone radical cystectomy (n=13), the elevated pre-operative levels of both HA (1978±530) and HAase (33±5.4) returned to normal in eight patients (P<0.0025). In four of the remaining five patients, the elevated urinary HA and HAase levels decreased by 2–5 fold. In patients who underwent bladder sparing treatment (n=12), the elevated pretreatment HA and HAase levels were 1405±500 and 167.5±22.5 respectively. These levels returned to normal in two of the three patients who underwent partial cystectomy and one patient, whose levels did not decrease, showed a recurrence at six months. Among seven patients who underwent TURBT+intravesical therapy, the urinary HA and HAase levels returned to normal in three patients, and two of these are tumor free at one year. In four out of seven patients the urinary HA and HAase levels did not return to normal; among these three showed a recurrence at 3–9 months and the fourth had persistent tumor. Two patients underwent TURBT alone; one patient's elevated HA and HAase levels did not decrease and the tumor recurred at six months. The other patient normalized and is tumor free at one year. The inventors also monitored 10 patients with a history of bladder cancer to evaluate the usefulness of HA-HAase test in monitoring recurrence. The HA-HAase test identified all six patients who had bladder cancer recurrence. The HA-HAase test detected recurrence of cancer in four patients 3–6 months prior to the cystoscopic detection of tumor.

In Study #2, the efficacy of the HA-HAase test to detect bladder cancer recurrence was evaluated in a double-blinded fashion. Seventy-one consecutive urine samples collected from 60 patients with a known histories of bladder cancer were examined by the HA-HAase test and the results were compared to the concurrent findings from cystoscopy, transurethral resection of the bladder tumor (TURBT) or cystectomy. Of the 50 patients who showed a clinical evidence of recurrence, 44 were detected by the HA-HAase test for an overall sensitivity of 88% (false negative rate 12%) and an accuracy of 84.5%. The accuracy of the HA-HAase test was further evaluated by monitoring 18 bladder cancer patients for three months to one year following an initial bladder sparing treatment. In this group of patients, the HA-HAase test detected 39 out of 42 recurrence episodes for an overall sensitivity of 92.9% (false negative rate 7.1%). Of the five false positives, recurrence was eventually confirmed in three instances 3–6 months later.

These studies show that the HA-HAase test is useful to monitor treatment efficacy and tumor recurrence. In conclusion, the HA-HAase test is a highly sensitive and specific non-invasive method to monitor both bladder cancer occurences and recurrences.

While the invention has been described in detail and with reference to specific embodiments thereof, it will be apparent to those of ordinary skill in the art that various changes and modifications can be made therein without departing from the spirit and scope of the invention as described and claimed.

What is claimed is:

1. A method of screening for bladder cancer in a patient, said method comprising the steps of:

obtaining a biological sample from the patient, wherein the sample is selected from the group consisting of bile, blood, plasma, serum, tissue extract, or urine;

quantitating the amount of total protein in the sample;

contacting the sample with a component of a standard assay method that selects for HA wherein the standard method is selected from the group consisting of an enzyme assay, immunoassay, radioassay, and competitive binding assay;

detecting the amount of HA in the sample by a detection method consistent with the standard assay method used in the contacting step; and thereby positively identifying the patient as having bladder cancer when the amount of HA of the patient is at least about 500 ng/mg total protein in the sample.

2. The method of claim 1, wherein the sample is obtained from a patient currently or previously treated for bladder cancer.

3. The method of claim 1, wherein the bladder cancer is selected from transitional cell carcinoma, squamous carcinoma, and adenocarcinoma.

4. A method of screening for intermediate-grade or high-grade bladder cancer in a patient, said method comprising the steps of:

obtaining a biological sample from the patient, wherein the sample is selected from the group consisting of bile, blood, plasma, serum, tissue extract, or urine;

quantitating the amount of total protein in the sample;

contacting the sample with a component of a standard assay method that selects for HAase wherein the standard method is selected from the group consisting of an enzyme assay, immunoassay, radioassay, and competitive binding assay;

detecting the amount of HAase in the sample by a detection method consistent with the standard assay method used in the contacting step; and thereby positively identifying the patient as having bladder cancer when the amount of HAase of the patient is at least about 10 milliunits/mg total protein in the sample.

5. The method of claim 4, wherein the sample is obtained from a patient currently or previously treated for bladder cancer.

6. The method of claim 4, wherein the bladder cancer is selected from transitional cell carcinoma, squamous carcinoma, and adenocarcinoma.

7. The method of claim 1 or 4, wherein the patient is identified as having low-grade bladder cancer when the amount of HA is at least about 500 ng/mg total protein and the amount of HAase is less than about 10 milliunits/mg total protein in the sample.

8. The method of claim 1 or 4 wherein the patient is identified as having intermediate-grade or high-grade bladder cancer when the amount of HA is at least about 500 ng/mg total protein and the amount of HAase is at least about 10 milliunits/mg total protein.

* * * * *